(12) United States Patent
Scriban et al.

(10) Patent No.: US 8,193,392 B2
(45) Date of Patent: Jun. 5, 2012

(54) METHOD FOR ENANTIOSELECTIVE SYNTHESIS OF PHOSPHORUS-STEREOGENIC PHOSPHINES

(75) Inventors: Corina Scriban, Cambridge, MA (US); David S. Glueck, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 63 days.

(21) Appl. No.: 11/996,008

(22) PCT Filed: Jul. 28, 2006

(86) PCT No.: PCT/US2006/029230
§ 371 (c)(1),
(2), (4) Date: Jan. 17, 2008

(87) PCT Pub. No.: WO2007/016264
PCT Pub. Date: Feb. 8, 2007

(65) Prior Publication Data
US 2008/0193357 A1 Aug. 14, 2008

(51) Int. Cl.
*C07F 9/02* (2006.01)
(52) U.S. Cl. ............. 568/17; 568/16; 423/299; 510/469
(58) Field of Classification Search .................. 568/8–9, 568/5, 13, 16, 17; 510/469; 423/299, 358
See application file for complete search history.

(56) References Cited

U.S. PATENT DOCUMENTS 3,389,183 A 6/1968 Hays
5,523,437 A * 6/1996 Hayashi et al. ................. 556/21

OTHER PUBLICATIONS

Dung et al. Phase transfer catalysts in the chemical modification of polymers. Part III. Preparation of unsymmetrical tertiary phosphine oxides. Bulletin de la Societe Chimique de France (1982) (-10, Pt. 2), 299-90. ISSN: 0037-8968.*

Palladium-Catalyzed Asymmetric Phosphination: Enantioselective Synthesis of a P-Chirogenic Phosphine Jillian R. Moncarz,, Natalia F. Laritcheva, and, David S. Glueck Journal of the American Chemical Society 2002 124 (45), 13356-13357.*
CAPLUS Accession No. 98:107909 1983.
Fleming et al., "A Simple Method for enriching the Enantiomeric Purity of a Functional Molecule already Rich in One Enantiomer", J. Chem. Soc., Chem. Commun. 1994 99-100.
Imamoto et al., "Synthesis and Reactions of Phosphine-Boranes. Synthesis of New Bidentate Ligands with Homochiral Phosphine Centers via Optically Pure Phosphine-Boranes", J. Am. Chem. 1990 112:5244-5252.
Kovacik et al., "Pt(Me-Duphos)-Catalyzed Asymmetric Hydrophosphination of Activated Olefins: Enantioselective Synthesis of Chiral Phosphines", Organometallics 2000 19:950-953.
Korff et al., "Preparatiobn of chiral triarylphosphines by Pd-catalysed asymmetric P-C cross-coupling", Chem. Commun. 2004 530-531.
Moncarz et al., "Palladium-Catalyzed Asymmetric Phosphination. Enantioselective Synthesis of PAMP-BH3, Ligand Effects on Catalysis, and Direct Observation of the Stereochemistry of Transmetalation and Reductive Elimination", Organometallics 2003 22:3205-3221.
Moncarz et al., "Palladium-Catalyzed Asymmetric Phosphination: Enantioselective Synthesis of a P-Chirogenic Phosphine", J. Am. Chem. Soc. 2002 124:13356-13357.
Pican et al., "Palladium catalysed enantioselective phosphination reactions using secondary phosphine-boranes and aryl iodide", Chem. Commun. 2005 2393-2395.

* cited by examiner

*Primary Examiner* — Stuart Hendrickson
*Assistant Examiner* — Richard M Rump
(74) *Attorney, Agent, or Firm* — Licata & Yurrell P.C.

(57) ABSTRACT

The present invention relates to a process for preparing an enantioenriched phosphorus-stereogenic, tertiary phosphine. Secondary phosphines are contacted with an alkyl halide and base in the presence of a chiral metal catalyst thereby producing the enantioenriched phosphorus-stereogenic, tertiary phosphine for subsequent use in homogeneous catalysis reactions.

2 Claims, No Drawings

METHOD FOR ENANTIOSELECTIVE SYNTHESIS OF PHOSPHORUS-STEREOGENIC PHOSPHINES

INTRODUCTION

This invention was made in the course of research sponsored by the National Science Foundation (Grant Numbers CHE-0111190 and CHE-0455715). The U.S. government may have certain rights in this invention.

BACKGROUND OF THE INVENTION

Chiral phosphines, valuable ligands for metal-catalyzed asymmetric reactions (Noyori *Asymmetric Catalysis in Organic Synthesis*; Wiley-Interscience: New York, 1994; Blaser and Schmidt, Eds. *Asymmetric Catalysis on Industrial Scale. Challenges, Approaches, and Solutions*; Wiley-VCH: Weinheim, 2004), are usually prepared either by resolution or by using a stoichiometric amount of a chiral auxiliary (Pietrusiewicz and Zablocka (1994) *Chem. Rev.* 94:1375-1411; Kagan and Sasaki, In: *The Chemistry of Organophosphorus Compounds*, F. R. Hartley, Ed., John Wiley and Sons: Chichester, England, 1990, Vol. 1, pp. 51-102). Metal-catalyzed asymmetric synthesis of these ligands has been carried out (Burk, et al. (1993) *J. Am. Chem. Soc.* 115:10125-10138; Hoge (2003) *J. Am. Chem. Soc.* 125:10219-10227; Shimizu, et al. (2003) *Adv. Synth. Catal.* 345:185-189; Marinetti and Genet (2003) *C. R. Chimie* 6:507-514. Enzymatic catalysis has also been employed: Shioji, et al. (2003) *Tetrahedron Lett.* 44:1103-1105; Kielbasinski, et al. (2003) *Tetrahedron: Asymmetry* 14:3379-3384; Kielbasinski, et al. (1994) *Tetrahedron Lett.* 35:7081-7084; Kagan, et al. (1994) *Bioorg. Med. Chem.* 2:15-21; Serreqi and Kazlauskas (1994) *J. Org. Chem.* 59:7609-7615 and P-stereogenic phosphines have been prepared via platinum-catalyzed hydrophosphination of activated alkenes (Kovacik, et al. (2000) *Organometallics* 19:950-953) and palladium-catalyzed phosphination of aryl halides (Moncarz, et al. (2002) *J. Am. Chem. Soc.* 124:13356-13357; Moncarz, et al. (2003) *Organometallics* 22:3205-3221; Korff and Helmchen (2005) *Chem. Commun.* 530-531; Pican and Gaumont (2005) *Chem. Commun.* 2393-2395).

Needed in the art is a catalytic process for preparing enantioenriched tertiary phosphines for use as ligands for homogeneous catalysis. The present invention meets this long felt need.

SUMMARY OF THE INVENTION

The present invention is a method for preparing an enantioenriched, phosphorus-stereogenic, tertiary phosphine. The method involves contacting a secondary phosphine with an alkyl-X moiety and base in the presence of a chiral metal catalyst thereby preparing an enantioenriched, phosphorus-stereogenic, tertiary phosphine. In particular embodiments, X of the alkyl-x moiety is a halide, tosylate, sulfonate, or other leaving group.

DETAILED DESCRIPTION OF THE INVENTION

Terminal metal phosphido complexes (M-PR$_2$) undergo rapid inversion at phosphorus (Rogers, et al. (1994) *Inorg. Chem.* 33:3104-3110). With a chiral ancillary ligand (L*), the complexes M(L*)(PRR') exist as mixtures of rapidly interconverting diastereomers (Moncarz, et al. (2002) supra) with different rates of nucleophilic reactivity. For example, it has been shown that alkylation of iron (Fe) complex 1 gives complete stereoselectivity at −95° C., because reaction with ethyl iodide (EtI) is faster than phosphorus inversion, but at 25° C. a 3.2:1 product ratio was observed because phosphorus inversion is competitive with alkylation, and the diastereomers of 1 react with EtI at comparable rates (Crisp, et al. (1989) *Organometallics* 8:2360-2367).

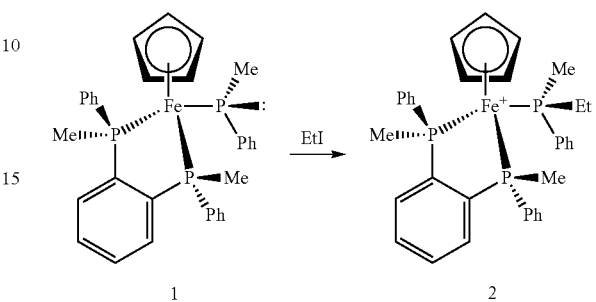

Such diastereoselective stoichiometric alkylation could be made catalytic if a tertiary phosphine complex like 2 could be converted to a starting phosphido complex like 1. To develop such reactions, several important hurdles must be overcome: the background reaction of a secondary phosphine with an alkyl halide electrophile has to be made much slower than the metal-catalyzed reaction; the equilibrium ratio of phosphido diastereomers and their relative reactivities with the alkyl halide electrophile has to be controlled; product inhibition has to be avoided; and the chiral ancillary ligand has to resist displacement from the metal by the excess phosphine substrate and products. A new catalytic process has now been found that resolves these issues by utilizing chiral metal complexes to catalyze asymmetric alkylation of secondary phosphines in up to >99% enantiomeric excess.

The process method of the instant invention provides for the conversion of a racemic secondary phosphine PHRR' to an enantioenriched tertiary phosphine PRR'R". The process involves treating the racemic secondary phosphine PHRR' with an electrophile R"X (wherein R" is alkyl and X is halide or other leaving group) and a base in the presence of a chiral metal catalyst such as a chiral platinum catalyst. This process is useful for generating chiral P-stereogenic tertiary phosphines, a valuable class of compounds employed as ligands for homogeneous catalysis in the production of fine chemicals and pharmaceutical agents (Johansson and Kann (2004) *Mini-Reviews in Organic Chemistry* 1:233-247; Crepy and Imamoto (2003) *Top. Curr. Chem.* 229:1-40). As used in the context of the present invention, tertiary phosphine is intended to include tertiary phosphines as well as di- or poly-tertiary phosphines. Likewise, in the context of the present invention, secondary phosphine is intended to include secondary phosphines as well as di- or poly-secondary phosphines and alkyl halide is intended to include an alkyl halide as well as dihaloalkanes or polyhaloalkanes.

The term stereoisomer refers to molecules that are made up of the same atoms connected by the same sequence of bonds, but have different three-dimensional structures. The term stereoisomer includes enantiomers, i.e., mirror image stereoisomers, cis-trans isomers, and diastereomers.

In the context of the instant invention, chiral refers to the stereochemical property of a molecule of being non-superimposable on its mirror image. A chiral molecule has no symmetry elements of the second kind, e.g., a mirror plane, a center of inversion, and a rotation-reflection axis. The two forms of a chiral molecule are known as enantiomers, wherein each molecule has a stereogenic center with the same substituents attached thereto, except that one molecule's stereogenic center is "R" and the other molecule's stereogenic center is "S". In the context of the instant invention, the stereogenic center is phosphorus. A collection containing equal amounts of the two enantiomeric forms of a chiral molecule is referred to as a racemic mixture or racemate.

The term diastereomers refers to non-enantiomeric isomers which arise when more than one stereocenter is present in a molecule.

A collection of molecules containing only one enantiomeric form of a chiral molecule is referred to as enantiopure, enantiomerically pure, or optically pure. A mixture containing predominantly one enantiomer is referred to as enantioenriched or enantiomerically enriched. Enantiopurity (i.e., the degree of enantioenrichment) is usually reported in terms of enantiomeric excess (ee), which is determined as: % ee= (major−minor)*100/(major+minor), wherein the term major refers to the amount of the more abundant enantiomer and the term minor refers to the amount of the less abundant enantiomer. For example, a sample containing S and R enantiomers in a ratio of 80:20 has an ee of 60% for the S enantiomer: ee=(S−R)*100/(S+R). In particular embodiments of the instant invention, a tertiary phosphine ligand produced in accordance with the instant methods has a high level of enantiopurity such that it is in about 9 to >99% ee. Alternatively stated, a tertiary phosphine ligand of the invention is in enantiomeric excess of greater than 5%, 10%, 20%, 30%, 40%, 50%, 60%, 70%, 80% or 90%. Optical activity can be measured using standard methods such as chiral high-performance liquid chromatography, circular dichroism, or by polarimetry or nuclear magnetic resonance spectroscopy on a diastereomeric derivative. The molecular structure and concentration of chiral molecules in the sample determines the amount of optical rotation. Each optically active substance has its own specific rotation as defined by Biot's law.

As used herein, each of R or R' can independently be a linear, branched or cyclic alkyl; substituted alkyl; aryl; substituted aryl; alkoxy; aryloxy; alkylthio; arylthio and the like. L is a neutral or charged ligand and M is metal. The abbreviations Me, Et, Ph, i-Pr, Cp, and Is represent methyl, ethyl, phenyl, isopropyl, cyclopentadienyl, and $2,4,6\text{-}(i\text{-}Pr)_3C_6H_2$, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists are well-known to one of ordinary skill in the art. Abbreviations used to describe various components of the process disclosed herein are defined for each component.

To carry out the method of the instant invention, a secondary phosphine, an alkyl halide, a base, and a chiral platinum or palladium catalyst are added to an inert solvent or inert solvent mixture. The reaction mixture is reacted at a temperature of from −100° C. to 100° C., or generally from −50° C. to 50° C., or more desirably at or less than 25° C., for a period of from 5 minutes to 5 weeks, or generally from 10 minutes to 70 hours, or more specifically from 15 minutes to 24 hours under anaerobic conditions (e.g., under an inert atmosphere of a gas such as nitrogen or argon).

Depending upon such factors as the solvent employed, the concentration of product, and the like, the catalyst can be separated from the product by filtration. The crude product can be freed of the solvent or the solvents (e.g., under vacuum) and subsequently purified by methods known to those skilled in the art and matched to the respective product, e.g. by recrystallization, distillation, sublimation, zone melting, melt crystallization or chromatography.

Solvents suitable for the method of the invention are, for example, ethers (e.g., diethyl ether, dimethoxyethane, diethylene glycol, dimethyl ether, tetrahydrofuran, dioxane, diisopropyl ether, tert-butyl methyl ether), hydrocarbons (e.g., hexane, iso-hexane, heptane, cyclohexane, benzene, toluene, xylene), alcohols (e.g., methanol, ethanol, 1-propanol, 2-propanol, ethylene glycol, 1-butanol, 2-butanol, tert-butanol), ketones (e.g., acetone, ethyl methyl ketone, iso-butyl methyl ketone), amides (e.g., dimethylformamide, dimethylacetamide, N-methylpyrrolidone), nitriles (e.g., acetonitrile, propionitrile, butyronitrile), water and mixtures thereof. Particularly suitable solvents are ethers (e.g., dimethoxyethane, tetrahydrofuran), hydrocarbons (e.g., cyclohexane, benzene, toluene, xylene), alcohols (e.g., ethanol, 1-propanol, 2-propanol), water and combinations thereof. In particular embodiments, solvents used in accordance with the instant method are toluene or tetrahydrofuran (THF) or combinations thereof.

As will be appreciated by the skilled artisan, the reactions of the present invention can be performed under a wide range of conditions, though it will be understood that the solvents and temperature ranges recited herein are not limitative and only correspond to a preferred mode of the process of the invention.

The reaction processes of the present invention can be conducted in continuous, semi-continuous or batch fashion. Likewise, the manner or order of addition of the reaction ingredients, catalyst and solvent are also not generally critical to the success of the reaction, and can be accomplished in any conventional fashion. Furthermore, one or more of the reactants can be immobilized or incorporated into a polymer or other insoluble matrix.

Secondary phosphine substrates which can be employed in the instant method include chiral secondary phosphine ligands, i.e., PHR(R'), and disecondary phosphine ligands, i.e., RP(H)-linker-PH(R). As used herein, a linker includes, but is not limited to, an alkyl or substituted alkyl chain, such as $(CH_2)_n$, or a benzene ring, such as ortho, meta, or para-$C_6H_4$, or a ferrocenyl group, such as $1,1'\text{-}C_5H_4FeC_5H_4$. In accordance with the instant invention, a secondary phosphine ligand can also include achiral secondary phosphines, i.e., $PHR_2$, and cyclic or linear poly-secondary phosphines of the form RP(H)-[linker-PH-linker]$_n$—PH(R) or cyclic analogues thereof. Suitable secondary phosphine substrates are exemplified herein and well-known in the art.

It is further contemplated that a primary phosphine $PH_2R$ can be used in combination with two different alkyl halide electrophiles, R'X and R"X, added sequentially to obtain an enantioenriched tertiary phosphine PRR'R". It is also contemplated that a protonated secondary phosphine (a phosphonium salt $[PH2RR']^+[A]^-$, where $[A]^-$ is an anion, such as $BF_4^-$, $SO_3CF_3^-$, etc.)] can be used as a substrate. In this case an additional equivalent of base would be required to deprotonate the phosphonium salt and generate the secondary phosphine.

The alkyl-X moiety of the instant method functions as an electrophile, i.e., a chemical moiety which accepts a pair of electrons from a nucleophile. In general, an alkyl-X moiety is intended to encompass benzyl-X or ring-fused benzyl-X (e.g., halomethylnaphthalene, halomethylanthracene, etc.), wherein X is a halide (e.g., Cl, Br, I), tosylate, sulfonate, or other leaving group. Likewise, di-electrophiles of the form $X\text{—}CH_2\text{—}C_6H_4\text{—}CH_2X$ (ortho, meta, or para) are also useful under appropriate conditions. Simple alkyl halides R"X, or di-alkyl halides such as X-linker-X are also contemplated, as are chiral benzylic (or alkyl) halides such as PhCH(Me)Br for use in combination with chiral or achiral secondary phosphines, or vinyl or allyl halides, or heterocycle-based alkyl halides, such as those formed from benzothiophenes, furans, etc. In particular embodiments, the alkyl-X moiety is benzyl-X, wherein X is a halide, tosylate, sulfonate or other leaving group. The substrate to alkyl-X ratio employed is generally in the range of 1:0.5 to 1:2 or more particularly stoichiometrically equivalent (i.e., 1:1). As such, the phosphorus to alkyl-X ratio is 1:1 and a disecondary phosphine substrate would require 2 equivalents of alkyl-X.

It is further contemplated that other electrophiles may be employed, such as aldehydes, ketones, alkenes, alkynes, and combinations thereof. Moreover, aryl halides activated by complexation to metal-ligand fragments, such as [CpFe(PhCl)]$^+$ or Cr(CO)$_3$(PhCl) can be used as electrophiles (Katagiri, et al. (2005) *Tetrahedron* 61: 4701-4707).

A base, as used in the context of the instant invention, is a chemical entity which is able to provide a pair of electrons to another chemical entity. Bases which are useful in the process of the invention include Brønsted bases and include alkali metal hydroxides (e.g., M=Li, K, or Na); alkaline earth metal hydroxides; alkaline earth metal carbonates; alkali metal hydrogen carbonates; alkaline earth metal acetates; alkaline earth metal alkoxides; alkaline earth metal phosphates; alkaline earth fluorides; ammonium salts (e.g., R$_4$N$^+$B$^-$, wherein B$^-$ is a Brønsted base, such as alkoxide, hydroxide, amide, and the like); and primary, secondary and tertiary amines. Examples of suitable bases include, but are not limited to, MOt-Bu, MOR, MOH, M$_2$CO$_3$, M$_3$PO$_4$, and NR$_3$. In particular embodiments, the base is sodium trimethylsilanolate (NaOSiMe$_3$). Base is used in approximately stoichiometric proportions to the substrate in the instant method. Large excesses of base are not necessary in order to obtain good yields of the desired products under mild reaction conditions. In some embodiments, the substrate to base ratio employed is in the range of 1:0.5 to 1:2. In particular embodiments, the ratio of substrate to base is equal (i.e., 1:1). As such, the phosphorus to base ratio is 1:1 and a disecondary phosphine substrate would require 2 equivalents of base.

Chiral metal catalysts M(chiral ligand) (Y)$_n$(Z)$_n$ based on one or more metals selected from Groups 3, 4, 5, 6, 7, 8, 9, 10, 11, and 12 of the Periodic Table of Elements are employed in the instant method to carry out the asymmetric phosphination. In some embodiments, M is Pt, Os, Ru, Ni, Fe, Ir, Rh, Co, or Pd. In other embodiments, M is Pt, Ni, Fe or Pd. In still further embodiments, M is Pt or Pd. In particular embodiments, a chiral Pt catalyst is used. The chiral ligand of the catalyst can be a monodentate, bidentate, or polydentate phosphine structure or any other type of chiral ligand, such as an amine, N-heterocyclic carbene, oxazoline, etc. Chiral phosphine ligands are particularly useful as chiral monophosphines and diphosphines (e.g., Tol-Binap, Binap, Duphos, H$_8$-Binap, BPE, Binapo, Biphemp, MeO-Biphep, Naphos, Bdpab, and the like) are readily available from commercial sources. For example, a catalyst based upon the chiral M(Duphos)(Y)(Z) precursor could employ any one of a family of commercial Duphos ligands (e.g., Me-Duphos or i-Pr-Duphos) in combination with any well-known Y and Z substituent including linear, branched or cyclic alkyl, aryl, halide groups, or combinations thereof. One of the Y or Z groups should be chosen to undergo substitution in the presence of a secondary phosphine and the base, so that the M-Y or M-Z bond (or both) can be converted into a M-PRR' bond. It is also contemplated that a secondary phosphine PHRR' can be one (or both) of Y and Z. In this case, the Pt catalyst precursor would be a cation and an additional equivalent of base would be required to deprotonate each secondary phosphine ligand.

The source of chirality in the metal complex catalyst need not be a neutral ligand, such as a phosphine, N-heterocyclic carbene, oxazoline, or the like. Instead, a chiral alkyl group such as (-)-menthyl, or a chiral alkoxide like OCH(Me)(Ph), or chiral amides, thiolates and the like can be employed. In some cases, the metal complex catalyst can contain more than one source of chirality, such as the complexes Pt(diphos*)((-)-menthyl)(Cl), where diphos* is a chiral diphosphine.

The selection of a catalytic precursor may be dependent upon suitable Y and Z groups which prevent cleavage of the M—Y bond. For example, a fluoroalkyl or fluoroaryl group selected as Y of Pd(chiral ligand) (Y) (Z) would be suitable for preventing cleavage of the Pd—Y bond. Moreover, it is contemplated that other catalyst precursors can be employed, e.g., Cp*Ru(chiral ligand)(Y) and CpFe(chiral diphosphine)(Y). As exemplified herein, catalytic precursors Pt(Me-Duphos)(Ph)(PMeIs), Pt(Me-Duphos)(I)(PMeIs), Pt(Me-Duphos) (PMeIs)$_2$, Pt(1-Pr-Duphos)(Ph)(PMeIs), Pt(Me-Duphos) (Ph)(Cl), Pt(1-Pr-Duphos)(Ph)(Cl), Pt(Me-Duphos)(Me)(Cl) Pt(Me-Duphos)(Cl)$_2$, Pt(Tol-Binap)(Ph)(Cl), Pt(Tol-Binap)(Me)(Cl) and Pd(Me-Duphos)(C$_6$F$_5$)(I) are particularly suitable for catalyzing asymmetric phosphination of secondary phosphine substrates. Advantageously, the amount of catalyst used in the process of the invention is low relative to the amount of substrate. Generally, the ratio of substrate to catalyst is in the range of 40:1 to 10:1. In particular embodiments, the substrate to catalyst ratio is 20:1. Alternatively, the amount of catalyst used is in the range of 1 to 15 mol %, or 2.5 to 10 mol %, or more specifically 5 mol %.

In addition to isolated, purified metal complexes as catalyst precursors, catalysts can be prepared in situ by assembly of suitable chiral ligands and metal complexes. For example, treatment of Pt(COD)(R)(Cl) (COD=cyclo-octadiene, R=Me or Ph; Clark and Manzer (1973) *J. Organomet. Chem.* 59:411-428) with a chiral diphosphine diphos* generates Pt(diphos*)(R)(Cl), which may be used directly to catalyze the asymmetric alkylation of a secondary phosphine or diphosphine.

When a secondary diphosphine such as 1,2-bis(phenylphosphino)ethane is used, $^{31}$P NMR spectroscopy on reaction mixtures can be conveniently used to measure the rac/meso ratio of the product. Thus, carrying out a series of reactions using different metal precursors, different chiral ligands, and different disecondary phosphine substrates is a rapid method to prepare and evaluate a library of P-stereogenic ditertiary phosphines. This combinatorial method is not limited with respect to the nature of the metal precursor, the chiral ligand, the substrates, or the analysis method; HPLC (high-performance liquid chromatography) on a chiral stationary phase, among other methods, could also be used to assess the diastereomeric excess and enantiomeric excess of the products in this catalyst screening approach.

Similar product libraries can be readily prepared by variation of a single parameter, such as the electrophile (benzyl halide). Thus, asymmetric alkylation of a secondary diphosphine, such as 1,2-bis(phenylphosphino)ethane, 1,2-bis(phenylphosphino)propane, 1,1'-bis(phenylphosphino)ferrocene, and the like, with a series of benzyl halides can be used to prepare a combinatorial library of P-stereogenic diphosphines. The rate of reaction and the diastereomeric excess and enantiomeric excess of the products can be rapidly assessed using NMR spectroscopy or other spectroscopic or chromatographic techniques.

Upon preparation of a tertiary phosphine, or a di- or polytertiary phosphine, the enantiomeric excess (and diastereomeric excess, for di- or polyphosphines) can be increased by a purification process, such as crystallization, sublimation, or chromatography. The purification may be carried out directly on the phosphine or on a derivative, such as the borane adduct (Ohff, et al. (1998) *Synthesis* 1391-1413), or the protonated salt (Netherton and Fu (2001) *Org. Lett.* 3:4295-4298)), which can in a subsequent step be converted to the phosphine.

To illustrate the utility of the process method of the instant invention, the thermally stable Pt complex 3 was used to catalyze the alkylation of PHMe(Is) (4) with the electrophile benzyl chloride in the presence of the base NaOSiMe$_3$ at room temperature (Scheme 1). The reaction was slow (on the order of weeks) but the catalyst was robust and the product PMeIs(CH$_2$Ph) (5) was formed in high yield with 70% ee. Under these conditions, the background reaction occurred only to the extent of ~20%.

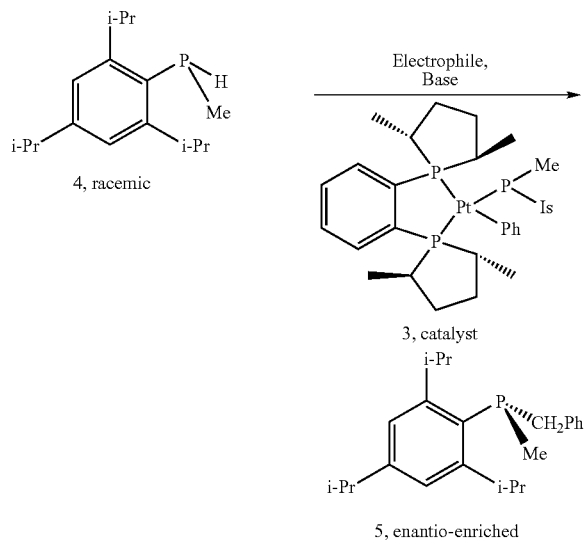

SCHEME 1

4, racemic 3, catalyst 5, enantio-enriched

Catalysis with benzyl bromide was more rapid (on the order of hours) with a similar ee (77%). Entries 3-5 in Table 1 show that analogous Pt-phosphido complexes also acted as catalyst precursors. Furthermore, air-stable halo precursors, entries 6-10 (Brunker, et al. (2005) *Organometallics* 24:2730-2746; Wicht, et al. (1998) *Organometallics* 17:1412-1419), were equally active and selective. Entries 6 and 7 indicate that ee improved with lower temperature. Tol-Binap (entries 11 and 12) was also an effective ligand and the Pd-complex, Pd(Me-Duphos) (C$_6$F$_5$)(I) (entry 13) was an active catalyst precursor.

TABLE 1

| Entry | Catalyst Precursor[a] | Time | Yield (%) | ee (%) |
|---|---|---|---|---|
| 1 | Pt(Me-Duphos)(Ph)(PMeIs) | 4 weeks | 99 | 70 |
| 2 | Pt(Me-Duphos)(Ph)(PMeIs) | 3 hours | 99 | 77 |
| 3 | Pt(Me-Duphos)(I)(PMeIs) | 4 hours | 92 | 31 |
| 4[b] | Pt(Me-Duphos)(PMeIs)$_2$ | 20 hours | 98 | 24 |
| 5 | Pt(i-Pr-Duphos)(Ph)(PMeIs) | 24 hours | 99 | −49 |
| 6 | Pt(Me-Duphos)(Ph)(Cl) | 1 hour | 95 | 75 |
| 7 | Pt(Me-Duphos)(Ph)(Cl) | 1 day[c] | 94 | 83 |
| 8 | Pt(i-Pr-Duphos)(Ph)(Cl) | 4 hours | 87 | −45 |
| 9 | Pt(Me-Duphos)(Me)(Cl) | 15 minutes | 79 | 38 |
| 10[b] | Pt(Me-Duphos)(Cl)$_2$ | <20 hours | 85 | 22 |
| 11 | Pt(Tol-Binap)(Ph)(Cl) | 1 day | 90 | 61 |
| 12 | Pt(Tol-Binap)(Me)(Cl) | 1 day | 63 | 52 |
| 13 | Pd(Me-Duphos)(C$_6$F$_5$) (I) | 1 day | 85 | 43 |

[a]5 mol % catalyst loading, base = NaOSiMe$_3$, solvent = toluene (entries 2-3) or THF. Benzyl bromide was used, except for entry 1 (benzyl chloride).
[b]2.5 mol % catalyst.
[c]The reagents were combined at −10° C. and the reaction was carried out at −25° C.

The instant method was also carried out employing a variety of commercially available benzylic halide substrates (Table 2). In addition to benzyl bromide, o-substitution of the benzyl phenyl group was tolerated (entries 1-2) as was an anthracenylmethyl group (entry 3). Secondary phosphines PHMe(Ar) with different aryl groups (entries 4-6) were acceptable substrates, and the dialkylphosphine PHMe(Men) (Men=(−)-menthyl, entry 7) was used. Secondary phenylphosphines with aryl (entries 8-9) or alkyl substituents (entries 10-11) were also employed.

The method of the instant invention can also be used to prepare enantiomerically enriched diphosphines using disecondary phosphine substrates (entries 12-15). These reactions selectively provide the rac, instead of the meso diastereomer, and the rac isomer is formed enantioselectively (Fleming and Ghosh (1994) *J. Chem. Soc., Chem. Commun.* 99-100).

Meta-substituted products (entries 14-15) are potential precursors for chiral pincer complexes (Williams, et al. (2001) *Helv. Chim. Acta* 84:3519-3530; Morales-Morales, et al. (2002) *J. Organomet. Chem.* 654:44-50), while the diphosphines formed in entries 12-13 are analogous to Knowles' industrially useful ligand DiPAMP (Knowles (2002), *Angew. Chem. Int. Ed.* 41:1998-2007).

TABLE 2[a]

| Entry | Substrate | Product | Yield (%) | Enantiopurity (% ee) |
|---|---|---|---|---|
| 1 | 2-I-C$_6$H$_4$CH$_2$Br | 2-I-C$_6$H$_4$CH$_2$PMeIs | 88 | 55 |
| 2 | 2-CN-C$_6$H$_4$CH$_2$Br | 2-CN-C$_6$H$_4$CH$_2$PMeIs | 86 | 50 |

TABLE 2ᵃ-continued

| Entry | Substrate | Product | Yield (%) | Enantiopurity (% ee) |
|---|---|---|---|---|
| 3 | 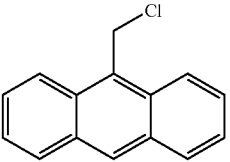 | 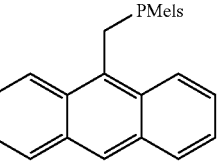 | 77 | 66 |
| 4 | PhCH₂Br | PMe(Phes)(CH₂Ph) | 86 | 81 |
| 5 | PhCH₂Br | PMe(Mes)(CH₂Ph) | 86 | 69 |
| 6 | PhCH₂Br | PMe(Ph)(CH₂Ph) | 84 | 35 |
| 7 | PhCH₂Br | PMe(Men)(CH₂Ph) | 87 | 56% de |
| 8 | PhCH₂Br | PPh(o-An)(CH₂Ph) | 85 | 9 |
| 9 | PhCH₂Br | PPh(Is)(CH₂Ph) | 27 | 22 |
| 10 | PhCH₂Br | PPh(Cy)(CH₂Ph) | 90 | 48 |
| 11 | PhCH₂Br | PPh(t-Bu)(CH₂Ph) | 74 | 42 |
| 12 | PhCH₂Br | 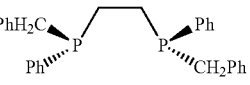 | 81 | 47% de 91% ee |
| 13 | PhCH₂Br | 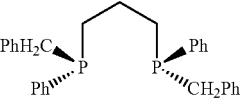 | 87 | 59% de 93% ee |
| 14 | PhCH₂Br | 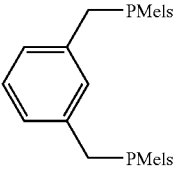 | 86 | 55% de 69% ee |
| 15 | PhCH₂Br | 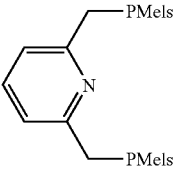 | 90 | 17% de 72% ee |

ᵃCatalyst precursor = Pt(Me-Duphos)(Ph)(Cl) (5 mol %), base = NaOSiMe₃.
Cy = cyclo-C₆H₁₁,
Phes = 2,4,6-Ph₃C₆H₂,
Mes = 2,4,6-Me₃C₆H₂,
o-An = o-MeOC₆H₄,
Men = (−)-menthyl.
de = diastereomeric excess.

The novel method for the catalytic asymmetric synthesis of P-stereogenic phosphines disclosed herein relies on the enhanced nucleophilicity and reduced inversion barrier in the diastereomeric Pt-phosphido intermediates. The scope of the reaction (i.e., the use of a plurality of alkyl-X electrophiles in combination with a plurality of secondary phosphines) and the ability to tune the catalyst by choice of the ancillary ligand (i.e., chiral diphosphine and Pt-Y group) provides a practical method for preparing enantioenriched P-stereogenic, tertiary phosphine ligands for use in homogeneous catalysis reactions.

EXAMPLE 1

Materials and Methods

Unless otherwise noted, all reactions and manipulations were performed in dry glassware under a nitrogen atmosphere at 20° C. in a dry box or using standard Schlenk techniques. Petroleum ether (bp 38-53° C.), ether, THF, toluene, and CH₂Cl₂ were dried using columns of activated alumina (Pangborn, et al. (1996) Organometallics 15:1518-1520). NMR spectra were recorded using Varian 300 or 500 MHz spectrometers (Varian, Palo Alto, Calif.). ¹H and ¹³C NMR chemical shifts are reported vs Me₄Si and were determined by reference to the residual ¹H and ¹³C solvent peaks. ³¹P NMR chemical shifts are reported vs H₃PO₄ (85%) used as an external reference. Coupling constants are reported in Hz, as absolute values unless noted otherwise. Unless indicated, peaks in NMR spectra are singlets. Elemental analyses were provided by Schwarzkopf Microanalytical Laboratory. Mass spectra were recorded at the University of Illinois Urbana-Champaign.

Unless otherwise noted, reagents were from commercial suppliers. The following compounds were made according to methods established in the art: Pt(COD)(Me)(Cl) and Pt(COD)(Ph)Cl) (COD=cyclooctadiene, Clark and Manzer (1973) *J. Organomet. Chem.* 59:411-428; Pt((R,R)-Me-Duphos)Cl$_2$ (Wicht, et al. (1998) *Organometallics* 17:1412-1419); Pt((R,R)-Me-Duphos)I$_2$ and Pt((R,R)-Me-Duphos)(Ph)(Cl) (Brunker, et al. (2005) *Organometallics* 24:2730-2746); (S)-{Pd[NMe$_2$CH(Me)C$_6$H$_4$] (Cl)}2 and (S)-{Pd [NMe$_2$CH(Me)C$_{10}$H$_6$] (Cl)}$_2$ (Tani, et al. (1977) *J. Am. Chem. Soc.* 99:7876-7886); Pd((R,R)-Me-Duphos) (C$_6$F$_5$)(I) (Drago and Pregosin (2002) *Organometallics* 21:1208-1215); Pt(R-Tol-Binap)(Me)(Cl) (Wicht et al. (1998) *Organometallics* 18:5141-5151); PHMe(Is) and PHPh(Is) (Brauer, et al. (1996) *Z. Naturforsch. B* 51:1183-1196); PHPh (o-MeOC$_6$H$_4$) (Vedejs and Donde (1997) *J. Am. Chem. Soc.* 119:9293-9294) and PHPh(t-Bu) (Wolfe and Livinghouse (1998) *J. Am. Chem. Soc.* 120:5116-5117). PH(t-Bu)(Ph) (BH$_3$) was prepared as reported, then deprotected with Et$_2$NH to yield the secondary phosphine. PH(Me)(Phes) and PHMe (Mes) (Ishiyama, et al. (2003) *Organometallics* 22:1096-1105) were prepared as for PHPh(Is) (Blank (2005) Ph.D. thesis, Dartmouth College, Hanover, N.H.). PHMe(Men) (Men=(−)-(menthyl) was prepared as described (Blank (2005) supra and Blank, et al. (2006) *Organometallics* 25: 1742-1748).

EXAMPLE 2

Preparation of the Catalyst Precursor Pt((R,R)-Me-Duphos)(Me)(Cl)

A solution of (R,R)-Me-Duphos (173 mg, 0.565 mmol) in CH$_2$Cl$_2$ (2 mL) was added dropwise to a solution of Pt(COD) (Me)(Cl) (200 mg, 0.565 mmol) in CH$_2$Cl$_2$ (3 mL) to give a pale-yellow solution. In the air, the solvent was removed under reduced pressure and the remaining crystals were washed with Et$_2$O (3×2 mL) and recrystallized from CH$_2$Cl$_2$/Et$_2$O at −25° C. to yield 247 mg (79%) of white crystals, suitable for single-crystal X-ray diffraction.

Anal. Calcd. for C$_{19}$H$_{31}$ClP$_2$Pt: C, 41.35; H, 5.66. Found: C, 41.31; H, 5.74. $^{31}$P{$^1$H} NMR (CDCl$_3$): δ 72.3 (d, J=4, J$_{Pt-P}$=1722), 61.4 (d, J=4, J$_{Pt-P}$=4065). $^1$H NMR (CDCl$_3$): δ 7.69-7.63 (m, 2H, Ar), 7.57-7.55 (m, 2H, Ar), 3.24-3.18 (m, 1H), 3.06-2.96 (m, 1H), 2.82-2.69 (m, 2H), 2.40-2.25 (m, 4H), 2.02-1.94 (m, 1H), 1.89-1.63 (m, 3H), 1.45-1.40 (dd, J=18, 7, 3H, Me), 1.29-1.24 (dd, J=18, 7, 3H, Me), 0.90-0.86 (dd, J=15, 7, 3H, Me), 0.86-0.82 (dd, J=15, 7, 3H, Me), 0.71-0.60 (dd, J=7, 2, J$_{Pt-H}$=53, 3H, Me). $^{13}$C{$^1$H} NMR (CDCl$_3$): δ 144.2 (dd, J 38, 49, quat), 142.6 (dd, J=25, 36, quat), 133.1 (d, J=13, Ar), 132.1 (dd, J=4, 15, Ar), 131.3-131.1 (m, Ar), 40.8 (d, J=26), 40.1 (d, J=39), 37.3-36.7 (m), 35.6 (d, J=26), 17.2 (3-line pattern, Me), 14.4 (d, J=2, Me), 14.1 (Me), 6.5 (dd, J=6, 97, Pt-Me).

EXAMPLE 3

Preparation of the Catalyst Precursor Pt(R-Tol-Binap)(Ph)(Cl)

A solution of (R)-Tol-Binap (94 mg, 0.23 mmol) in CH$_2$Cl$_2$ (2 mL) was added dropwise to a solution of Pt(COD)(Ph)(Cl) (153 mg, 0.23 mmol) in CH$_2$Cl$_2$ (3 mL) to give a pale-yellow solution. In the air, the solvent was removed under reduced pressure and the remaining crystals were washed with diethyl ether (3×2 mL) and recrystallized from CH$_2$Cl$_2$ and diethyl ether at −25° C. to yield 200 mg (90%) of white crystals.

A sample was dissolved in CD$_2$Cl$_2$ and the solvent was removed under vacuum to give a white solid solvate for elemental analysis. Anal calcd. for C$_{54}$H$_{45}$ClP$_2$Pt.3.5CD$_2$Cl$_2$: C, 53.51; H, 3.51. Found: C, 54.14; H, 3.86.

$^{31}$P{$^1$H} NMR (CDCl$_3$): δ 17.0 (d, J=18, J$_{Pt-P}$=1630), 13.0 (d, J=18, J$_{Pt-P}$=4358). $^1$H NMR (CDCl$_3$): δ 7.83 (dd, J=11, 9, 1H, Ar), 7.74 (dd, J=11, 8, 2H, Ar), 7.63 (dd, J=9, 2, 1H, Ar), 7.55 (d, J=9, 2H, Ar), 7.43-7.27 (m, 10H, Ar), 7.16-7.11 (m, 3H, Ar), 7.05-7.01 (m, 2H, Ar), 6.83 (d, J=9, 1H, Ar), 6.78 (dd, J=8, 3, 2H, Ar), 6.72 (td, J=7, 2, 2H, Ar), 6.62 (t, J=9, 2H, Ar), 6.45 (d, J=8, 2H, Ar), 6.37 (broad, 3H, Ar), 2.42 (3H, CH$_3$), 2.20 (3H, CH$_3$), 1.98 (3H, CH$_3$), 1.96 (3H, CH$_3$). $^{13}$C{$^1$H} NMR (CDCl$_3$): δ 140.2 (d, J=2, Ar), 139.8 (d, J=3, Ar), 139.7 (d, J=2, Ar), 139.5 (d, J=3, Ar), 139.1 (d, J=4, Ar), 139.0 (d, J=4, Ar), 137.8 (m, Ar), 135.7 (d, J=11, Ar), 135.3 (d, J=13, Ar), 134.9 (d, J=10, Ar), 133.7 (d, J=2, Ar), 133.6 (d, J=2, Ar), 133.4 (d, J=7, Ar), 133.2 (d, J=9, Ar), 131.7 (Ar), 131.4 (Ar), 130.9 (Ar), 128.9 (d, J=11, Ar), 128.4-128.1 (m, Ar), 128.0-127.6 (m, Ar), 127.2 (d, J=8, Ar), 126.8 (d, J=11, Ar), 126.4 (Ar), 126.3 (Ar), 126.0 (Ar), 123.2 (Ar), 122.7 (Ar), 122.4 (Ar), 122.3 (Ar), 21.7 (CH$_3$), 21.32 (CH$_3$), 21.29 (CH$_3$), 21.24 (CH$_3$).

EXAMPLE 4

Preparation of the Catalyst Precursor Pt((R,R)-Me-Duphos)(Ph)(PMeIs)

PHMeIs (141 mg, 0.56 mmol) was added with a microsyringe to a stirring slurry of Pt[(R,R)-Me-Duphos](Ph)(Cl) (346 mg, 0.56 mmol) in toluene (10 mL). NaOSiMe$_3$ (63.3 mg, 0.56 mmol) in toluene (10 mL) was added to the reaction mixture. As soon as Pt[(R,R)-Me-Duphos](Ph)(Cl) reacted, the mixture turned yellow; it was stirred for ~3 hours. The slurry was filtered through CELITE®, and the yellow filtrate was concentrated under vacuum. Petroleum ether was added to the yellow residue, yielding yellow crystals, which were washed further with petroleum ether, and dried under vacuum, yielding 415.5 mg (89%) of yellow crystals suitable for X-ray crystallography.

Anal calcd for C$_{40}$H$_{59}$P$_3$Pt: C, 58.03; H, 7.18. Found: C, 56.29; H, 7.41. Elemental analyses for carbon were consistently low, perhaps due to decomposition of the air-sensitive complex: Anal calcd for C$_{40}$H$_{59}$P$_3$PtO: C, 56.93; H, 7.05. HRMS m/z calcd. for C$_{40}$H$_{60}$P$_3$Pt (MH$^+$): m/z 828.3569. Found, 828.3571. $^1$H NMR (C$_6$D$_6$): δ 8.07 (t, J=6, J$_{Pt-H}$=51, 1H, Ph ortho), 7.68 (t, J=7, J$_{Pt-H}$=51, 1H, Ph ortho), 7.37 (t, J=7, 1H, Ar), 7.29 (t, J=7, 1H, Ar), 7.21-7.18 (t, J=6, 1H, Ar), 7.16 (2H, Is), 7.13-7.11 (m, 1H, Ar), 7.04 (t, J=7, 1H, Ar), 6.97-6.90 (m, 2H, Ar), 5.16 (broad, 2H, CH, Is), 3.01-2.94 (m, 1H, CH), 2.89-2.81 (m, 1H, CH), 2.36-2.28 (m, 1H, CH), 2.17-2.08 (m, 1H, CH), 1.81-1.67 (m, 3H), 1.62 (dd, J=17, 6, 6H, Me), 1.51 (d, J=7, 6H, Me), 1.48-1.43 (m, 3H, P-Me), 1.40 (dd, J=18, 7, 6H, Me), 1.28 (d, J=8, 3H, Me), 1.27 (d, J=7, 3H, Me), 0.99 (qd, J=13, 5, 1H), 0.90-0.80 (m, 1H), 0.64 (dd, J=14, 7, J$_{Pt-H}$=53, 3H, Me), 0.58 (dd, J=15, 8, 3H, Me). $^{13}$C{$^1$H} NMR (C$_6$D$_6$): δ 154.7 (quat, Ar), 147.7 (quat, Ar), 147.2 (quat, Ar), 143.9-143.5 (m, Ar), 139.9 (Ph ortho), 137.6 (broad, Ph ortho), 133.1 (dd, J=86, 14, Duphos), 130.0 (d, J=78, Duphos), 128.2-127.7 (m, Ar overlapping with C$_6$D$_6$ signals), 122.2 (Ph para), 120.5 (broad, 2C, Is meta), 44.1 (d, J=30, CH Duphos), 41.9-41.4 (m, CH Duphos), 37.8 (CH$_2$), 36.3 (CH$_2$), 35.5 (overlapping CH$_2$ and CH, Is), 34.7 (CH, Is), 34.3 (CH, Is), 32.8-32.1 (overlapping m and d, J=42, 2CH Duphos), 27.2 (broad, CH$_3$, Is), 24.5 (CH$_3$, Is), 22.6 (CH$_3$, Is), 18.1 (dd, J=20, 9, CH$_3$, Duphos), 15.6 (d, J=9, CH$_3$, Duphos), 14.8 (d, J=3, CH$_3$, Duphos), 14.5 (d, J=2, CH$_3$, Duphos), 12.5-12.0 (m, P—CH$_3$). $^{31}$P{$^1$H} NMR (C$_6$D$_6$): δ 58.3 (broad, J$_{Pt-P}$=1869), 57.6 (dd, J=133, 8, J$_{Pt-P}$=1621), −51.8 (broad d, J=133, J$_{Pt-P}$=899).

EXAMPLE 5

Preparation of the Catalyst Precursor Pt((R,R)-1-Pr-Duphos)(Ph)(Cl)

A solution of (R,R)-i-Pr-Duphos (293 mg, 0.7 mmol) in CH$_2$Cl$_2$ (2 mL) was added dropwise to a solution of Pt(COD)(Ph)(Cl) (291 mg, 0.7 mmol) in CH$_2$Cl$_2$ (3 mL) to give a colorless solution. In the air, the solvent was removed under reduced pressure and the remaining crystals were washed with diethyl ether (3×2 mL) and recrystallized from CH$_2$Cl$_2$ and diethyl ether at −25° C. to yield 350 mg (70%) of white Pt[(R,R)-i-Pr-Duphos](Ph)(Cl) crystals suitable for X-ray crystallography. Anal. Calcd. for C$_{32}$H$_{49}$ClP$_2$Pt: C, 52.92; H, 6.80. Found: C, 52.79; H, 6.41.

$^{31}$P{$^1$H} NMR (C$_6$D$_6$): δ 58.8 (d, J=3, J$_{Pt-P}$=1627), 47.2 (d, J=3, J$_{Pt-P}$=3944). $^1$H NMR (C$_6$D$_6$): δ 7.96 (t, J=7, J$_{Pt-H}$=36, 2H), 7.36-7.32 (m, 3H), 7.20-7.16 (m, 1H), 7.10 (t, J=8, 1H), 7.07-7.00 (m, 2H), 3.38-3.21 (m, 1H), 3.08-3.00 (m, 1H), 2.85-2.76 (m, 1H), 2.55-2.45 (m, 1H), 2.29-2.21 (m, 1H), 2.13-2.03 (m, 2H), 2.02-1.92 (m, 2H), 1.75-1.36 (m, 6H), 1.19 (d, J=7, 3H, Me), 1.15 (d, J=7, 3H, Me), 1.12-1.03 (m, 1H), 0.99 (d, J=7, 3H, Me), 0.91 (d, J=7, 3H, Me), 0.80 (d, J=7, 3H, Me), 0.71 (d, J=7, 3H, Me), 0.64 (d, J=7, 3H, Me), 0.56 (d, J=7, 3H, Me). $^{13}$C{$^1$H} NMR (C$_6$D$_6$): δ 161.5 (dd, J=120, 8, quat, Pt-Ph), 145.3 (dd, J=45, 38, quat Ar), 144.3 (dd, J=32, 24, quat Ar), 139.3 (Ph), 133.9 (d, J=13, Ar), 133.1 (dd, J=15, 4, Ar), 131.4-131.2 (m, Ar), 131.1-130.9 (m, Ar), 128.6 (d, J=7, Ph), 123.6 (Ph), 54.7 (d, J=23, CH), 53.8 (d, J=38, CH), 8.0 (d, J=24, CH), 46.6 (d, J=34, CH), 31.9, 31.7, 1.4, 30.5 (d, J=8), 30.4 (d, J=7), 30.0 (d, J=5), 9.4 (d, J=2), 28.4 (m), 26.3 (d, J=7, Me), 26.1 (d, J=, Me), 25.5 (d, J=6, Me), 24.6 (d, J=6, Me), 22.2 (d, J=11, Me), 21.9 (d, J=9, Me), 21.5 (d, J=6, Me), 21.3 (d, J=8, Me).

EXAMPLE 6

Preparation of the Catalyst Precursor Pt((R,R)-i-Pr-Duphos)(Ph)(PMeIs)

PHMeIs (112.5 mg, 0.45 mmol) was added with a microsyringe to a stirring slurry of Pt[(R,R)-i-Pr-Duphos](Ph)(Cl) (327 mg, 0.45 mmol) in THF (20 mL). NaOSiMe$_3$ (50.5 mg, 0.45 mmol) in toluene (10 mL) was added to the reaction mixture. The mixture turned yellow immediately. The solvent was removed under vacuum, and toluene (20 mL) was added to the residue. The toluene slurry was filtered through CELITE®, and the yellow filtrate was concentrated under vacuum. Petroleum ether was added to the yellow residue. The yellow solution was stored at −25° C. for 24 hours, yielding yellow crystals suitable for X-ray crystallography, and a yellow solution. The yellow crystals were further washed with petroleum ether (3×5 mL) and dried under vacuum, yielding 300 mg (71%) of yellow crystals, as a mixture of two diastereomers a and b.

Anal. Calcd. for C$_{48}$H$_{75}$P$_3$Pt: C, 61.32; H, 8.04. Found: C, 59.14; H, 7.90. Satisfactory analyses for C could not be obtained, perhaps because of the air-sensitivity of the complex. (Anal. Calcd. for C$_{48}$H$_{75}$P$_3$PtO: C, 60.30; H, 7.91). Mass spectroscopy was also consistent with oxidation. HRMS (FAB) calcd for C$_{48}$H$_{76}$OP3Pt$^+$ (M(O)H$^+$): m/z 956.4771. Found: m/z 956.4668.

The following NMR spectra at 21° C. are reported as a mixture of diastereomers unless otherwise indicated. $^{31}$P{$^1$H} NMR (THF-d$_8$): δ 54.3 (d, J=131, J$_{Pt-P}$=1654), 50.8 (broad, J$_{Pt-P}$=1818), −60.0 (broad). $^1$H NMR (THF-d$_8$): δ 7.88-7.86 (m, 1H, Ar, Duphos), 7.83-7.80 (m, 1H, Ar, Duphos), 7.57 (broad, 1H, Ph ortho), 7.48-7.43 (m, 2H, Ar, Duphos), 7.39 (broad t, J=7, 1H, J$_{Pt-H}$=49, Ph ortho), 6.98 (broad t, J=8, 1H, Ph meta), 6.94 (broad, 1H, Ph para), 6.90 (2H, Is meta), 6.72 (broad t, J=8, 1H, Ph meta), 4.68 (broad, 2H, CH, Is), 2.83-2.71 (m, 2H, overlapping CH Duphos+CH Is), 2.70-2.62 (broad, 1H, CH Duphos), 2.45-2.33 (m, 2H, 2CH Duphos), 2.30-2.16 (broad m, 1H, CH Duphos), 1.99-1.75 (m, 5H, CH+CH$_2$), 1.75-1.68 (m, 2H, CH$_2$), 1.64-1.55 (m, 2H, CH$_2$), 1.49 (qd, J=13, 5, 2H, CH Duphos), 1.25-1.18 (m, 18H, CH$_3$), 1.05 (broad, 3H, CH$_3$), 0.96-0.82 (m, 9H, overlapping CH$_3$ Duphos and P-Me), 0.68-0.62 (m, 9H, overlapping CH$_3$), 0.49 (broad, 3H, CH$_3$), 0.38 (broad, 3H, CH$_3$)—. $^{13}$C{$^1$H} NMR (THF-d$_8$): δ 161.4 (m, Pt-C, quat Ph), 155.0 (broad, quat Is), 149.0-148.5 (m, quat Duphos), 147.8 (quat Is), 145.2-144.7 (m, quat Duphos), 144.2 (m, quat Is), 140.3 (broad, Ph ortho), 139.2 (Ph ortho), 135.5 (d, J=15, Ar, Duphos), 134.3 (d, J=12, Ar, Duphos), 131.3 (m, Ar, Duphos), 130.8 (m, Ar, Duphos), 128.2 (d, J=6, Ph meta), 127.8 (m, Ph para), 122.2 (Ph meta), 121.1 (Is), 57.2 (d, J=24, CH, Duphos), 55.9 (d, J=25, CH, Duphos), 50.1 (broad m, CH, Duphos), 46.1 (d, J=23, CH Duphos), 35.3 (CH, Is), 33.7 (d, J=17, CH, Is), 32.5 (CH, Duphos), 31.6 (m, CH, Duphos), 31.1 (d, J=6, CH$_2$), 30.9-30.5 (m, CH, Duphos), 30.1-29.8 (m, CH, Duphos), 29.8 (d, J=8, CH$_2$), 29.2 (CH$_2$, Duphos), 27.9 (CH$_3$), 26.9 (d, J=4, CH$_3$), 26.5 (d, J=2, CH$_3$), 25.1 (d, J=6, CH$_3$), 24.6 (m, CH$_3$, Is), 22.3 (d, J=11, CH$_3$), 22.2 (d, J=11, CH$_3$), 21.1 (d, J=6, CH$_3$), 20.0 (broad, CH$_3$), 12.8 (broad m, P—CH$_3$).

EXAMPLE 7

Preparation of the Catalyst Precursor Pt((R,R)-Me-Duphos)(I)(PMeIs)

PHMeIs (91 mg, 0.36 mmol) was added with a microsyringe to a stirring slurry of Pt[(R,R)-Me-Duphos]I$_2$ (275 mg, 0.36 mmol) in toluene (10 mL). NaOSiMe$_3$ (40.8 mg, 0.36 mmol) in toluene (10 mL) was added to the reaction mixture. The mixture turned yellow, and the solution became homogeneous after 10 minutes. The slurry was filtered through CELITE®, and the yellow filtrate was concentrated under vacuum. Petroleum ether was added to the yellow residue. The solution was stored at −25° C. for 24 hours, yielding yellow crystals suitable for X-ray crystallography and a yellow solution. The yellow crystals were further washed with petroleum ether (3×5 mL) and dried under vacuum, yielding 250 mg (78%) of yellow crystals, as a mixture of 2 diastereomers a and b (a:b=16:1 at −40° C.). The following NMR spectra are reported as a mixture of two diastereomers.

HRMS m/z calcd. for C$_{34}$H$_{55}$IP$_3$Pt (MH$^+$) 877.2188. Found, 877.1935. Anal. calcd. for C$_{34}$H$_{54}$IP$_3$Pt: C, 46.53; H, 6.20. Found: C, 35.09; H, 5.19. The poor analytical results presumably stem from decomposition of the air-sensitive sample. $^{31}$P{$^1$H} NMR (21° C., toluene-d$_8$): δ 64.5 (broad d, J=117, J$_{Pt-P}$=1559), 54.4 (broad, J$_{Pt-P}$=3943), −68.3 (broad, J$_{Pt-P}$=842). $^{31}$P{$^1$H} NMR (−40° C., toluene-d$_8$): δ 65.8 (d, J=113, J$_{Pt-P}$=1633, b), 64.0 (dd, J=113, 17, J$_{Pt-P}$=1575, a), 65.0 (broad, J$_{Pt-P}$=3876, b), 54.1 (dd, J=21, 17, J$_{P-tP}$=3954, a), −42.5 (d, J=110, J$_{Pt-P}$=935, b), −69.6 (dd, J=113, 21, J$_{Pt-P}$=820, a). $^1$H NMR (21° C., toluene-d$_8$): δ 7.25-7.19 (m, 1H, Ar), 7.18-7.12 (m, 3H, Ar), 7.08-7.04 (m, 2H, Ar), 5.21 (broad, 2H, CH), 3.97-3.87 (m, 1H, CH), 2.87-2.80 (m, 1H, CH), 2.77-2.60 (broad, 3H), 2.58-2.49 (m, 2H), 2.36 (broad, 1H), 2.22-1.80 (m, 5H), 1.60 (dd, J=18, 7, 3H, CH$_3$), 1.48 (d, J=8, 3H, CH$_3$), 1.45 (d, J=7, 6H, 2CH$_3$), 1.38 (d, J=7, 6H, 2CH$_3$), 1.29 (d, J=7, 6H, 2CH$_3$), 0.86 (d, J=7, 3H, CH$_3$), 0.54 (dd, J=15, 7, 3H, CH$_3$), 0.51 (dd, J=14, 7, 3H, CH$_3$).

EXAMPLE 8

Preparation of the Catalyst Precursor Pt((R,R)-Me-Duphos)(PMeIs)$_2$

PHMeIs (120 mg, 0.48 mmol) was added with a microsyringe to a stirring slurry of Pt[(R,R)-Me-Duphos]Cl$_2$ (137 mg, 0.24 mmol) in toluene (10 mL). NaOSiMe$_3$ (53.8 mg, 0.48 mmol) in toluene (10 mL) was added to the reaction mixture. The mixture turned orange, and the solution became homogeneous after 30 minutes. The slurry was filtered through CELITE®, and the orange filtrate was concentrated under vacuum. Petroleum ether was added to the yellow residue. The solution was stored at −25° C. for 24 hours, yielding yellow crystals suitable for X-ray crystallography and a yellow solution. The yellow crystals were further washed with petroleum ether (3×5 mL) and dried under vacuum, yielding 195 mg (81%) of yellow crystals.

A spectroscopically pure bulk sample of 5 was not produced. Satisfactory elemental analyses could not be obtained for this material, perhaps because of its air sensitivity. Anal. Calcd. for C$_{50}$H$_{80}$P$_4$Pt: C, 60.04; H, 8.06. Found: C, 58.32; H, 8.11. These results are consistent with oxidation at both phosphorus centers: Anal. Calcd. for C$_{50}$H$_{80}$O$_2$P$_4$Pt: C, 58.18; H, 7.81. Mass spectroscopy was also consistent with oxidation: HRMS m/z calcd for C$_{50}$H$_{81}$P4PtO$_2$ (MO$_2$H)$^+$ 1032.4849. Found: m/z 1032.4847.

$^1$H NMR (THF-d$_8$, 21° C.): δ 7.82-7.74 (m, 2H, Ar), 7.54-7.48 (m, 2H, Ar), 6.92 (broad, 4H, Ar), 5.00 (broad, 4H, CH), 2.87-2.72 (m, 4H), 2.65-2.35 (broad, 2H), 2.28-2.10 (m, 2H), 2.10-1.70 (m, 6H), 1.62-1.54 (m, 12H, Me), 1.26-1.13 (overlapping m, 36H, CH$_3$), 0.55 (dd, J=25, 12, 6H, CH$_3$). $^{31}$P{$^1$H} NMR (C$_6$D$_6$, 21° C.): δ 57.1 (broad), −56.9 (broad).

EXAMPLE 9

General Procedure for Catalytic Reaction of Benzyl Halides with Secondary Phosphines To a secondary phosphine (0.1 mmol) in 0.2 mL of solvent (toluene or THF) was added NaOSiMe$_3$ (11.2 mg, 0.1 mmol) suspended in 0.2 mL of solvent. The mixture was added to the catalyst precursor (0.005 mmol, 5 mol %) in 0.1 mL of solvent. The reaction mixture was transferred to an NMR tube. Benzyl halide (0.1 mmol) was added via microliter syringe, and the reaction mixture was monitored by $^{31}$P NMR spectroscopy. After the reaction went to completion, the catalyst and the sodium halide were removed from the reaction mixture on a silica column (14 cm height, 1 cm diameter), using a 9:1 petroleum ether:THF mixture as eluent. The catalyst and the sodium halide did not elute. The solvent was removed under vacuum, and the tertiary phosphines were dissolved in 0.5 mL of C$_6$D$_6$ for spectroscopic characterization.

EXAMPLE 10

Determination of ee

The C$_6$D$_6$ solution of tertiary phosphines was added to (S)-{Pd[NMe$_2$CH(Me)C$_6$H$_4$] (μ-Cl)}$_2$ (0.12 mmol, 69.6 mg) and the ee was determined by integration of the $^{31}$P NMR signals of the diastereomers (Table 3).

TABLE 3

| Example | Phosphine | δ ($^{31}$P)$^a$ (ppm) |
|---|---|---|
| 12, 14 | benzyl-PMeIs | 14.1, 14.8$^b$ |
| 16 | 2-iodobenzyl-PMeIs | 18.2, 18.6 |
| 18$^c$ | 2-cyanobenzyl-PMeIs | 16.9, 17.1 |
| 20 | 9-anthracenylmethyl-PMeIs | 13.0, 13.5 |
| 22 | benzyl-PMePhes | 15.7, 11.1 |
| 24 | benzyl-PMeMes | 14.9, 17.2 |
| 26 | benzyl-PPhMe | 20.5, 22.9 |
| 28 | benzyl-PMeMen | 26.8, 20.8 |
| 30 | benzyl-PPhCy | 51.1, 46.6 |
| 32 | benzyl-PPh(t-Bu) | 57.1, 55.5 |
| 34 | benzyl-PPh(o-An) | 32.1, 34.9 |
| 36 | benzyl-PPhIs | 18.3, 20.7 |

TABLE 3-continued

| Example | Phosphine | δ ($^{31}$P)$^a$ (ppm) |
|---|---|---|
| 38 | BnPPh–PPhBn (1,3-propylene bridge with two benzyl, two phenyl groups) | 37.7, 39.0 (b) 38.7, 38.0 (a) |
| 40 | BnPPh–(CH$_2$)$_3$–PPhBn | 28.3, 35.3 (b) 34.9, 31.3 (a) |
| 42 | 1,3-bis(PMeIs-CH$_2$)benzene | 14.0, 12.2 (a) 15.0, 14.1 (b) |
| 44 | 2,6-bis(PMeIs-CH$_2$)pyridine | 14.3, 13.3 (a) 12.5, 12.2 (b) |

$^a$The chemical shift of the major diastereomer is listed first. For diphosphines, chemical shifts for the rac isomer are listed first, followed by those for the meso isomer.
$^b$In one case (entry 7, Table 1), ee was determined using an analogous method with the (S)-{Pd[NMe$_2$CH(Me)C$_{10}$H$_6$](Cl)}$_2$ complex. The resulting $^{31}$P NMR shifts were δ 12.9 and 15.3.
$^c$Peaks were not baseline resolved, so the error in the reported ee is larger than in the other examples.

EXAMPLE 11

Reaction of Benzyl Chloride with PHMeIs in the Absence of a Catalyst

To PHMeIs (25 mg, 0.1 mmol) in 0.2 mL of toluene was added NaOSiMe$_3$ (11.2 mg, 0.1 mmol) suspended in 0.3 mL of toluene. The reaction mixture was transferred to an NMR tube. Benzyl chloride (11.6 μL, 13 mg, 0.1 mmol) was added via microliter syringe, and the reaction mixture was monitored by $^{31}$P NMR spectroscopy. Formation of a white precipitate was observed as the reaction progressed. After 1 month conversion was ~20%. In addition to the product PMeIs(CH$_2$Ph) (δ −41.6), another peak (δ 40.8) was observed, with selectivity 69%.

EXAMPLE 12

Catalytic Reaction of Benzyl Chloride with PHMeIs for the Synthesis of P(Me)(Is)(CH$_2$Ph)(5)

To PHMeIs (25 mg, 0.1 mmol) in 0.2 mL of toluene was added NaOSiMe$_3$ (11.2 mg, 0.1 mmol) suspended in 0.2 mL of toluene. The mixture was added to Pt(Me-Duphos)(Ph)(PMeIs) (4.1 mg, 0.005 mmol) as the catalyst precursor (5 mol %) in 0.1 mL of toluene. The reaction mixture was transferred to an NMR tube. Benzyl chloride (11.6 μL, 13 mg, 0.1 mmol) was added via microliter syringe, and the reaction mixture was monitored by $^{31}$P NMR spectroscopy. An increasing amount of white precipitate was observed as the reaction progressed. The reaction went to completion in ~1 month. The catalyst and NaCl were removed from the reaction mixture on a silica column (14 cm height, 1 cm diameter), using a 9:1 petroleum ether:THF mixture as eluent. The catalyst and NaCl did not elute. The solvent was removed under vacuum and 34 mg (99% yield) of a colorless oil (70% ee) was obtained. The tertiary phosphine was dissolved in 0.5 mL of C$_6$D$_6$ for spectroscopic characterization.

HRMS m/z calcd. for C$_{23}$H$_{34}$P$^+$ (MH$^+$) 341.2398. Found, 341.2400. $^{31}$P{$^1$H} NMR (C$_6$D$_6$): δ −40.0 (selectivity 100%). $^1$H NMR (C$_6$D$_6$): δ 7.18 (broad, 1H, Ar), 7.16 (broad, 1H, Ar), 7.13 (d, J 2, 2H, Is), 7.09 (t, J=7, 2H, Ar), 7.03-6.99 (m, 1H, Ar), 4.15-4.08 (m, 2H, CH), 3.27 (d, J=14, 1H, CH$_2$), 3.15 (d, J=14, 1H, CH$_2$), 2.79-2.73 (m, 1H, CH), 1.41 (d, J=7, 3H, P—CH$_3$), 1.33 (d, J=7, 6H, CH$_3$, i-Pr), 1.21 (d, J=7, 6H, CH$_3$, i-Pr), 1.20 (d, J=7, 6H, CH$_3$, i-Pr) $^{13}$C{$^1$H} NMR (C$_6$D$_6$): δ 156.3 (d, J=14, quat), 150.9 (d, J=1, quat), 140.4 (d, J=11, quat), 131.0 (d, J=26, quat), 29.8 (d, J=6, Ar), 129.0 (d, J=2, Ar), 126.3 (d, J=3, Ar), 122.7 (d, J=4, Is), 37.2 (d, J=18, CH, i-Pr), 35.0 (CH, i-Pr), 31.9 (d, J=21, CH$_2$), 25.5 (2CH$_3$, Is), 25.3 (2CH$_3$, Is), 24.4 (2CH$_3$, Is), 12.0 (d, J=21, P—CH$_3$).

EXAMPLE 13

Reaction of Benzyl Bromide with PHMeIs in the Absence of Catalyst

To PHMeIs (25 mg, 0.1 mmol) in 0.2 mL of solvent (toluene or THF) was added NaOSiMe$_3$ (11.2 mg, 0.1 mmol) suspended in 0.3 mL of solvent. The reaction mixture was transferred to an NMR tube. Benzyl bromide (12 μL, 17 mg, 0.1 mmol) was added via microliter syringe, and the reaction mixture was monitored by $^{31}$P NMR spectroscopy. Formation of a white precipitate was observed as the reaction progressed. In toluene, after 3 weeks, conversion was ~20% and selectivity 41% (other peaks δ 35.7, 35.5, −55.1, −58.4, −83.9). In THF, after 2 weeks conversion was ~33% and selectivity 49% (other peaks 5 30.7, −59.4, −62.6, −88.9, −111.5).

EXAMPLE 14

Catalytic Reaction of Benzyl Bromide with PHMeIs Using Different Catalyst Precursors To PHMeIs (25 mg, 0.1 mmol) in 0.2 mL of solvent (toluene or THF) was added NaOSiMe$_3$ (11.2 mg, 0.1 mmol) suspended in 0.2 mL of solvent. The mixture was added to Pt(Duphos)(Y) (Z) or Pd(Me-Duphos)(C$_6$F$_5$)(I) (0.005 mmol; Table 4) as the catalyst precursor (5 mol %) in 0.1 mL of solvent. The reaction mixture was transferred to an NMR tube. Benzyl bromide (12 μL, 17 mg, 0.1 mmol) was added via microliter syringe, and the reaction mixture was monitored by $^{31}$P NMR spectroscopy. An increasing amount of white precipitate was observed as the reaction progressed. The catalyst and NaBr were removed from the reaction mixture on a silica column (14 cm height, 1 cm diameter), using a 9:1 petroleum ether:THF mixture as eluent. The catalyst and NaBr did not elute. The solvent was removed under vacuum, and the tertiary phosphine was dissolved in 0.5 mL of C$_6$D$_6$ for spectroscopic characterization.

TABLE 4

| Catalyst Precursor | Amount of Catalyst (mg)[a] | Time | Yield (%) | ee (%) |
|---|---|---|---|---|
| Pt(Me-Duphos)(Ph)(PMeIs)[b] | 4.1 | 3 h | 99 | 77 |
| Pt(Me-Duphos)(I)(PMeIs)[c] | 4.4 | 4 h | 92 | 31 |
| Pt(Me-Duphos)(PMeIs)$_2$[c,d] | 2.5 | 20 h | 98 | 24 |
| Pt(i-Pr-Duphos)(Ph)(PMeIs)[c] | 4.7 | 24 h | 99 | −49 |
| Pt(Me-Duphos)(Ph)(Cl)[c] | 3.1 | 1 h | 95 | 75 |
| Pt(Me-Duphos)(Ph)(Cl)[c,e] | 3.1 | 24 h | 94 | 83 |
| Pt(i-Pr-Duphos)(Ph)(Cl)[c] | 3.6 | 4 h | 87 | −45 |
| Pt(Me-Duphos)(Me)(Cl)[c] | 2.8 | 15 min | 79 | 38 |
| Pt(Me-Duphos)Cl$_2$[c,d] | 1.4 | <20 h | 85 | 22 |
| Pt(Tol-Binap)(Ph)(Cl)[c] | 4.9 | 24 h | 90 | 61 |
| Pt(Tol-Binap)(Me)(Cl)[c] | 4.6 | 24 h | 63 | 52 |
| Pd(Me-Duphos)(C$_6$F$_5$)(I)[c] | 3.5 | 24 h | 85 | 43 |

[a]General procedure for the reactions was 5 mol % catalyst loading, 1 equiv of benzyl bromide and NaOSiMe$_3$ per phosphine. Time for completion of the reaction (as determined by $^{31}$P NMR monitoring) is reported in h (hours) or min (minutes).
[b]In toluene.
[c]In THF.
[d]2.5 mol % catalyst.
[e]Reagents were combined at −10° C. and, after 1 hour, the reaction was carried out at −25° C.

EXAMPLE 15

Reaction of 2-Iodobenzyl Bromide with PHMeIs in the Absence of Catalyst

To PHMeIs (25 mg, 0.1 mmol) in 0.2 mL of toluene was added NaOSiMe$_3$ (11.2 mg, 0.1 mmol) suspended in 0.2 mL of toluene. The mixture was added to C$_6$H$_4$(CH$_2$Br)(o-I) (29.7 mg, 0.1 mmol) in 0.1 mL of toluene. The reaction mixture was transferred to an NMR tube and monitored by $^{31}$P NMR spectroscopy. An increasing amount of white precipitate was observed as the reaction progressed. After 2 days the conversion was 48% and selectivity 82% (other peaks δ41.1, −53.1, −56.4, −88.3).

EXAMPLE 16

Catalytic Reaction of 2-Iodobenzyl Bromide with PHMeIs

To PHMeIs (25 mg, 0.1 mmol) in 0.1 mL of toluene was added NaOSiMe$_3$ (11.2 mg, 0.1 mmol) suspended in 0.2 mL of toluene. The mixture was added to Pt(Me-Duphos)(Ph)(PMeIs) (4.1 mg, 0.005 mmol) as the catalyst precursor (5 mol %) in 0.1 mL of toluene and to C$_6$H$_4$(CH$_2$Br) (o-I) (29.7 mg, 0.1 mmol) in 0.1 mL of toluene. The reaction mixture was transferred to an NMR tube and monitored by $^{31}$P NMR spectroscopy. An increasing amount of white precipitate was observed as the reaction progressed. The reaction went to completion in ~1 day. The catalyst and NaBr were removed from the reaction mixture on a silica column (14 cm height, 1 cm diameter), using a 9:1 petroleum ether:THF mixture as eluent. The catalyst and NaBr did not elute. The solvent was removed under vacuum and 41 mg (88% yield) of white crystals (55% ee) was obtained. The tertiary phosphine was dissolved in 0.5 mL of C$_6$D$_6$ for spectroscopic characterization.

HRMS m/z calcd. for C$_{23}$H$_{33}$PI$^+$ (MH$^+$) 466.1365. Found, 467.1361. $^{31}$P{$^1$H} NMR (C$_6$D$_6$): δ −40.1 (selectivity 97%, other peak −53.3). $^1$H NMR (C$_6$D$_6$): δ 7.70 (broad d, J=8, 1H, Ar), 7.16 (d, J=2, 2H, Is), 6.95 (dt, J=8, 2, 1H, Ar), 6.82 (broad t, J=8, 2H, Ar), 6.46 (broad t, J=8, 1H, Ar), 4.22-4.15 (m, 2H, CH, i-Pr), 3.55 (d, J=13, 1H, CH$_2$), 3.35 (d, J=13, 1H, CH$_2$), 2.79-2.74 (m, 1H, CH, i-Pr), 1.48 (d, J=8, 3H, P—CH$_3$), 1.34 (d, J=7, 6H, CH$_3$, i-Pr), 1.27 (d, J=7, 6H, CH$_3$, i-Pr), 1.21 (d, J=7, 6H, CH$_3$, i-Pr). $^{13}$C{$^1$H} NMR (C$_6$D$_6$): δ 156.3 (d, J=14, quat), 151.1 (d, J=1, quat), 143.6 (d, J=12, quat), 140.2 (d, J=2, quat), 130.5 (d, J=8, Ar), 128.7 (m, Ar, obscured by C$_6$D$_6$ peaks), 128.0 (d, J=3, Ar), 122.8 (d, J=4, Is), 102.2 (d, J=6, C—I), 41.9 (CH, i-Pr), 41.7 (CH, i-Pr), 35.0 (CH, i-Pr), 32.0 (d, J=21, CH$_2$), 25.7 (2CH$_3$, Is), 25.3 (2CH$_3$, Is), 24.4 (2CH$_3$, Is), 11.9 (d, J=21, P—CH$_3$).

EXAMPLE 17

Reaction of 2-cyanobenzyl bromide with PHMeIs in the Absence of a Catalyst

To PHMeIs (25 mg, 0.1 mmol) in 0.2 mL of THF was added NaOSiMe$_3$ (11.2 mg, 0.1 mmol) suspended in 0.2 mL of THF. The mixture was added to 2-(bromomethyl)benzonitrile) (19.6 mg, 0.1 mmol) in 0.1 mL of THF. The reaction mixture was transferred to an NMR tube and monitored by $^{31}$P NMR spectroscopy. An increasing amount of white precipitate was observed as the reaction progressed. After 20 hours the conversion was 78% and selectivity 71% (other peaks δ 35.6, 28.8, −53.8, −84.6).

EXAMPLE 18

Catalytic Reaction of 2-cyanobenzyl bromide with PHMeIs

To PHMeIs (25 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF and to 2-(bromomethyl)benzonitrile) (19.6 mg, 0.1 mmol) in 0.1 mL of THF. The reaction mixture was transferred to an NMR tube and monitored by $^{31}$P NMR spectroscopy. An increasing amount of white precipitate was observed as the reaction progressed. The reaction went to completion in ~15 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 31 mg (86% yield) of colorless liquid (~50% ee, see Table 3) was obtained. The tertiary phosphine was dissolved in 0.5 mL of C$_6$D$_6$ for spectroscopic characterization.

HRMS m/z calcd. for C$_{24}$H$_{33}$NP$^+$ (MH$^+$) 366.2351. Found, 366.2339. $^{31}$P{$^1$H} NMR (C$_6$D$_6$): δ −35.6 (selectivity 100%). $^1$H NMR (C$_6$D$_6$): δ 7.15 (d, J=3, 2H, Is), 7.08 (dd, J=8, 1, 1H, Ar), 6.89 (broad d, J=8, 1H, Ar), 6.80 (td, J=8, 2, 1H, Ar), 6.57 (broad t, J=8, 1H, Ar), 4.22-4.12 (m, 2H, CH, i-Pr), 3.66 (d, J=13, 1H, CH$_2$), 3.18 (dd, J$_{HH}$=13, J$_{PH}$=2, 1H, CH$_2$), 2.78-2.71 (m, 1H, CH, i-Pr), 1.44 (d, J$_{PH}$=7, 3H, P—CH$_3$), 1.37 (d, J=7, 6H, CH$_3$, i-Pr), 1.28 (d, J=7, 6H, CH$_3$, i-Pr), 1.20 (d, J=7, 6H, CH$_3$, i-Pr). $^{13}$C{$^1$H} NMR (C$_6$D$_6$): δ 156.4 (d, J=14, quat), 151.4 (d, J=1, quat) 144.8 (d, J=11, quat), 133.1 (d, J=2, Ar), 132.5 (d, J=2, Ar), 130.4 (d, J=7, Ar), 126.5 (d, J=3, Ar), 122.9 (d, J=4, Is), 113.7 (d, J=5, CN), 35.4 (d, J=21, 2CH, i-Pr), 35.0 (CH, i-Pr), 32.0 (d, J=21, CH$_2$), 25.6 (2CH$_3$, Is), 25.3 (2CH$_3$, Is), 24.4 (2CH$_3$, Is), 11.6 (d, J=21, P—CH$_3$).

EXAMPLE 19

Reaction of 9-Chloromethyl Anthracene with PHMeIs in the Absence of a Catalyst

To PHMeIs (25 mg, 0.1 mmol) in 0.1 mL of toluene was added NaOSiMe$_3$ (11.2 mg, 0.1 mmol) suspended in 0.2 mL of toluene and 9-chloromethyl anthracene (22.6 mg, 0.1 mmol) in 0.1 mL of toluene. The reaction mixture was transferred to an NMR tube and monitored by $^{31}$P NMR spectroscopy. Formation of a white precipitate was observed as the reaction progressed. After 1 week, conversion was ~36% and selectivity 72% (other peaks δ 36.9 (major), −22.4, −51.9, −53.2, −55.3, −55.5, −56.5, −84.7).

EXAMPLE 20

Catalytic Reaction of 9-Chloromethyl Anthracene with PHMeIs

To PHMeIs (25 mg, 0.1 mmol) in 0.1 mL of toluene was added NaOSiMe$_3$ (11.2 mg, 0.1 mmol) suspended in 0.2 mL of toluene. The mixture was added to Pt(Me-Duphos)(Ph) (PMeIs) (4.1 mg, 0.005 mmol) as the catalyst precursor (5 mol %) in 0.1 mL of toluene and 9-chloromethyl anthracene (22.6 mg, 0.1 mmol) in 0.1 mL of toluene. The reaction mixture was transferred to an NMR tube, and the reaction mixture was monitored by $^{31}$P NMR spectroscopy. An increasing amount of white precipitate was observed as the reaction progressed. The reaction went to completion in 1 week. The catalyst and NaCl were removed from the reaction mixture on a silica column (14 cm height, 1 cm diameter), using a 9:1 petroleum ether:THF mixture as eluent. The catalyst and NaCl did not elute. The solvent was removed under vacuum to give the tertiary phosphine as a yellow solid (34 mg, 77% yield, 66% ee). It was dissolved in 0.5 mL of C$_6$D$_6$ for spectroscopic characterization.

HRMS m/z calcd. for C$_{31}$H$_{38}$P$^+$ (MH$^+$) 441.2711. Found, 441.2691. $^{31}$P{$^1$H} NMR (C$_6$D$_6$): δ −36.2 (selectivity 98%, other peak −53.3). $^1$H NMR (C$_6$D$_6$): δ 8.27 (broad, 1H, Ar), 8.26 (broad, 1H, Ar), 8.12 (broad, 1H, Ar), 7.84 (broad, 1H, Ar), 7.82 (m, 1H, Ar), 7.30-7.23 (m, 4H, Ar), 7.21 (d, J=3, 2H, Is), 4.43 (d, J=14, J$_{P-H}$=3, 1H, CH$_2$), 4.27-4.19 (m, 2H, i-Pr), 4.16 (d, J=14, 1H, CH$_2$), 2.84-2.79 (m, 1H, CH, i-Pr), 1.53 (d, J=8, 3H, P—CH$_3$), 1.34 (d, J=7, 6H, CH$_3$, i-Pr), 1.27 (d, J=7, 6H, CH$_3$, i-Pr), 1.26 (d, J=7, 6H, CH$_3$, i-Pr). $^{13}$C{$^1$H} NMR (C$_6$D$_6$): δ 156.1 (d, J=14, quat, P-Is), 151.2 (d, J=1, quat), 134.2 (d, J=11, quat), 132.8 (d, J=28, quat), 132.7 (d, J=3, quat), 130.6 (d, J=5, quat), 130.0 (Ar), 126.61-125.58 (m), 125.8 (d, J=1, Ar), 125.79 (Ar), 125.5 (Ar), 122.9 (d, J=4, Is), 35.1 (CH, i-Pr), 32.3 (d, J=22, CH$_2$), 29.4 (d, J=21, CH, i-Pr), 25.8 (2CH$_3$, Is), 25.3 (2CH$_3$, Is), 24.5 (2CH$_3$, Is), 13.4 (d, J=23, P—CH$_3$).

EXAMPLE 21

Reaction of Benzyl Bromide with PHMePhes in the Absence of a Catalyst

To PHMePhes (35.2 mg, 0.1 mmol) in 0.2 mL of THF was added NaOSiMe$_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. No reaction was observed after 30 minutes.

EXAMPLE 22

Catalytic Reaction of Benzyl Bromide with PHMePhes

To PHMePhes (35.2 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. An increasing amount of white precipitate was observed as the reaction progressed. The reaction went to completion in ~30 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 38 mg (86% yield) of colorless liquid (81% ee) was obtained. The tertiary phosphine was dissolved in 0.5 mL of C$_6$D$_6$ for spectroscopic characterization.

HRMS m/z calcd. for C$_{32}$H$_{28}$PO$^+$ (MOH$^+$) 459.1878. Found, 459.1860. $^{31}$P{$^1$H} NMR (C$_6$D$_6$): δ −22.2 (selectivity 100%). $^1$H NMR (C$_6$D$_6$): δ 7.50 (d, J=2, 2H, Ar), 7.41-7.38 (m, 5H, Ar), 7.20-7.10 (m, 10H, Ar), 6.99-6.96 (m, 2H, Ar), 6.92 (d, J=8, 1H, Ar), 6.82 (d, J=8, 2H, Ar), 2.92 (dd, J=13, J$_{PH}$=4, 1H, CH$_2$), 2.56 (dd, J=13, J$_{PH}$=2, 1H, CH$_2$), 0.66 (d, J$_{PH}$=6, 3H, P—CH$_3$). $^{13}$C{$^1$H} NMR (C$_6$D$_6$): δ 150.1 (d, J=14, quat), 144.3 (d, J=4, quat), 140.8, 140.6, 139.4 (d, J=8), 135.9 (d, J=35), 130.7 (d, J=3, Ar), 130.3, 129.9 (d, J=6, Ar), 129.47, 129.35 (d, J=1, Ar), 128.8 (d, J=1), 128.7 (d, J=3), 128.4, 127.8 (d, J=5), 126.2 (d, J=3, Ar), 37.8 (d, J=19, CH$_2$), 11.6 (d, J=20, P—CH$_3$).

EXAMPLE 23

Reaction of Benzyl Bromide with PHMeMes in the Absence of a Catalyst

To PHMeMes (17 mg, 0.1 mmol) in 0.2 mL of THF was added NaOSiMe$_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. No reaction was observed after 30 minutes.

EXAMPLE 24

Catalytic Reaction of Benzyl Bromide with PHMeMes

To PHMeMes (17 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. An increasing amount of white precipitate was observed as the reaction progressed. The reaction went to completion in ~30 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 22 mg (86% yield) of colorless liquid (69% ee) was obtained. The tertiary phosphine was dissolved in 0.5 mL of C$_6$D$_6$ for spectroscopic characterization.

HRMS m/z calcd. for C$_{17}$H$_{22}$P$^+$ (MH$^+$) 257.1459. Found, 257.1441. $^{31}$P{$^1$H} NMR (C$_6$D$_6$): δ −33.5 (selectivity 98%; other peaks δ 28.5, −14.0). $^1$H NMR (C$_6$D$_6$): δ 7.10-6.98 (m, 5H, Ar), 6.71 (broad, 2H, Ar), 3.12 (dd, J=13, J$_{PH}$=1, 1H, $CH_2$), 3.02 (dd, J=13, $J_{PH}$=3, 1H, $CH_2$), 2.44 (6H, $CH_3$), 2.07 (3H, $CH_3$), 1.30 (d, $J_{PH}$=6, 3H, P—$CH_3$). $^{13}C\{^1H\}$ NMR ($C_6D_6$): δ 144.9 (d, J=15, quat), 139.9 (d, J=8, quat), 139.1 (d, J=1, quat), 131.5 (d, J=26, Ar), 130.5 (d, J=4, Ar), 129.7 (d, J=6, Ar), 128.8 (d, J=2, Ar), 126.2 (d, J=3, Ar), 35.7 (d, J=17, $CH_2$), 23.8 (d, J=19, 2$CH_3$), 21.3 ($CH_3$), 10.9 (d, J=19, P—$CH_3$).

EXAMPLE 25

Reaction of Benzyl Bromide with PHMePh in the Absence of a Catalyst

To PHMePh (12.4 mg, 0.1 mmol) in 0.2 mL of THF was added $NaOSiMe_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}P$ NMR spectroscopy. Formation of a white precipitate was observed as the reaction progressed. After 1 day the conversion was 97% and the selectivity 60% (other peaks δ 27.4, −39.7, −43.2).

EXAMPLE 26

Catalytic Reaction of Benzyl Bromide with PHMePh

To PHMePh (12.4 mg, 0.1 mmol) in 0.2 mL of THF was added $NaOSiMe_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 μL, 17 mg, 0.1 mmol) was added via microliter syringe, and the reaction mixture was monitored by $^{31}P$ NMR spectroscopy. An increasing amount of white precipitate was observed as the reaction progressed. The reaction went to completion in less than 30 minutes. The catalyst and NaBr were removed from the reaction mixture on a silica column (14 cm height, 1 cm diameter), using a 9:1 petroleum ether:THF mixture as eluent. The catalyst and NaBr did not elute. The solvent was removed under vacuum and 18 mg (84% yield) of a colorless oil (35% ee) was obtained. The tertiary phosphine was dissolved in 0.5 mL of $C_6D_6$ for spectroscopic characterization.

$^{31}P\{^1H\}$ NMR ($C_6D_6$): δ −29.1. $^{13}C\{^1H\}$ NMR ($C_6D_6$): δ 140.8 (d, J=17, quat Ar), 138.4 (d, J=5, quat Ar), 132.3 (d, J=18, Ar), 129.8 (d, J=5, Ar) 128.9 (d, J=15, Ar), 128.82 (Ar), 128.81 (Ar), 126.3 (d, J=2), 39.0 (d, J=17, $CH_2$), 10.8 (d, J=17, P-Me). $^1H$ NMR ($C_6D_6$): δ 7.34-7.30 (m, 2H, Ar), 7.13-7.06 (m, 5H, Ar), 7.02-6.99 (m, 1H, Ar), 6.96-6.94 (m, 2H, Ar), 2.89 (dd, J=13, 3, 1H, $CH_2$), 2.72 (d, J=13, 1H, $CH_2$), 1.02 (d, J=4, Me). These NMR data were consistent with the literature reports for this phosphine (Payne and Stephan (1980) *Can. J. Chem.* 58:15-21).

EXAMPLE 27

Reaction of Benzyl Bromide with PHMe(Men) in the Absence of a Catalyst

To PHMeMen (9.3 mg, 0.05 mmol) in 0.2 mL of THF was added $NaOSiMe_3$ (5.6 mg, 0.05 mmol) suspended in 0.3 mL of THF. The reaction mixture was transferred to an NMR tube. Benzyl bromide (6 μL, 17 mg, 0.05 mmol) was added via microliter syringe, and the reaction mixture was monitored by $^{31}P$ NMR spectroscopy. Formation of a white precipitate was observed as the reaction progressed. After 30 minutes the conversion was 8%.

EXAMPLE 28

Catalytic Reaction of Benzyl Bromide with PHMe(Men)

To PHMeMen (18.6 mg, 0.1 mmol) in 0.1 mL of THF was added $NaOSiMe_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 μL, 17 mg, 0.1 mmol) was added via microliter syringe, and the reaction mixture was monitored by $^{31}P$ NMR spectroscopy. An increasing amount of white precipitate was observed as the reaction progressed. The reaction went to completion in ~10 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 24 mg (87% yield) of colorless liquid (56% de) was obtained. The tertiary phosphine was dissolved in 0.5 mL of $C_6D_6$ for spectroscopic characterization.

HRMS m/z calcd. for $C_{18}H_{30}PO^+$ ($MOH^+$) 293.2034. Found, 293.2022. The following NMR spectra are reported as a mixture of two diastereomers a and b (a:b=3.5:1, 56% de) unless otherwise indicated.

$^{31}P\{^1H\}$ NMR ($C_6D_6$): δ −30.7 (b), −31.0 (a) (selectivity 100%). $^1H$ NMR ($C_6D_6$): δ 7.23-7.19 (broad m, 2H, Ar), 7.16-7.11 (m, 2H, Ar), 7.05-7.00 (broad m, 1H, Ar), 2.73 (dd, J=13, $J_{PH}$=3, 1H, $CH_2$, a), 2.72-2.66 (m, 1H, CH), 2.64 (d, J=13, 1H, $CH_2$, b), 2.57 (d, J=13, 1H, $CH_2$, b), 2.41 (dd, J=13, $J_{PH}$=3, 1H, $CH_2$, a), 1.80-1.76 (m, 1H, CH, a), 1.75-1.71 (m, 1H, CH, b), 1.69-1.64 (m, 1H, CH), 1.64-1.59 (m, 1H, CH), 1.27-1.21 (m, 1H, $CH_2$), 1.19-1.10 (m, 1H, $CH_2$), 1.09-1.02 (m, 1H, $CH_2$), 1.01-0.93 (m, 1H, $CH_2$), 0.92 (d, J=7, 3H, $CH_3$, a), 0.91 (d, J=7, 3H, $CH_3$, b), 0.88 (d, J=8, 1H, $CH_2$), 0.85 (dd, J=7, $J_{PH}$=1, 3H, $CH_3$), 0.84 (dd, J=7, $J_{PH}$=1, 3H, $CH_3$), 0.80 (d, $J_{PH}$=5, 3H, P—$CH_3$). $^{13}C\{^1H\}$ NMR ($C_6D_6$) δ 140.1 (d, J=8, quat), 129.96 (d, J=6, Ar, a), 129.85 (d, J=6, Ar, b), 128.99 (d, J=1, Ar, b), 128.96 (d, J=1, Ar, a), 126.3 (d, J=2, Ar, b), 126.2 (d, J=2, Ar, a), 45.8 (d, J=9, CH, a), 45.6 (d, J=11, CH, b), 39.6 ($CH_2$, a), 39.4 ($CH_2$, b), 35.9 (CH, a), 35.8 (CH, b), 35.10 (d, J=4, $CH_2$, a), 35.05 (d, J~5, $CH_2$, b, overlapping the 35.10 peak), 34.3 (d, J=1, CH, a), 34.1 (CH, b), 31.9 (d, J=20, P—$CH_2$), 28.25 (d, J=21, CH, a), 28.14 (d, J=22, CH, b), 26.2 (d, J=6, $CH_2$, a), 26.1 (d, J=7, $CH_2$, b), 23.32 ($CH_3$, i-Pr, b), 23.28 ($CH_3$, i-Pr, a), 22.12 ($CH_3$, i-Pr, b), 22.05 ($CH_3$, i-Pr, a), 15.8 (d, J=2, $CH_3$, a), 15.7 (d, J=2, $CH_3$, b), 9.1 (d, J=20, P—$CH_3$, a), 5.5 (d, J=23, P—$CH_3$, b).

EXAMPLE 29

Reaction of Benzyl Bromide with PHPh(Cy) in the Absence of a Catalyst

To PHPhCy (19 mg, 0.1 mmol) in 0.2 mL of THF was added $NaOSiMe_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}P$ NMR spectroscopy. Formation of a white precipitate was observed as the reaction progressed. After 2 days the conversion was 45% and the selectivity 65% (in addition to PPh(Cy)(CH$_2$Ph), another peak at 34 ppm was observed).

EXAMPLE 30

Catalytic Reaction of Benzyl Bromide with PHPh(Cy)

To PHPhCy (19 mg, 0.1 mmol) in 0.2 mL of THF was added NaOSiMe$_3$ (11.2 mg, 0.1 mmol) suspended in 0.2 mL of THF. The mixture was added to M(Me-Duphos)(Y)(Z) (0.005 mmol; Table 5) as the catalyst precursor (5 mol %) in 0.1 mL of THF. The reaction mixture was transferred to an NMR tube. Benzyl bromide (12 µL, 17 mg, 0.1 mmol) was added via microliter syringe, and the reaction mixture was monitored by $^{31}$P NMR spectroscopy. An increasing amount of white precipitate was observed as the reaction progressed. The catalyst and NaBr were removed from the reaction mixture on a silica column (14 cm height, 1 cm diameter), using a 9:1 petroleum ether:THF mixture as eluent. The catalyst and NaBr did not elute. The solvent was removed under vacuum and the tertiary phosphine was dissolved in 0.5 mL of C$_6$D$_6$ for spectroscopic characterization.

TABLE 5

| Catalyst precursor | Mass (mg) | Time | Selectivity (%) | Yield (%) | ee (%) |
|---|---|---|---|---|---|
| Pt(Me-Duphos)(Ph)(Cl) | 3.1 | 1 hour | 99, other peaks δ −12.1, 53.9 | 93 | 48 |
| Pd(Me-Duphos)(C$_6$F$_5$)(I) | 3.5 | 1 day | 49, other peaks δ −14.9, −23.3 | 90 | −18 |

The phosphine PPh(Cy)(CH$_2$Ph) is a known compound (Albert, et al. (1999) *Organometallics* 18:3511-3518) and $^{31}$P (δ −4.2 (C$_6$D$_6$), lit. −6.1 (CDCl$_3$)), $^1$H, and $^{13}$C NMR data were consistent with those reported in a different solvent. The ee was determined by the general method: $^{31}$P{$^1$H} NMR (C$_6$D$_6$): δ 51.1, 46.6, (48% ee). The solvent was removed from this sample under vacuum, and the residue was redissolved in CDCl$_3$ for direct comparison to established results (Albert, et al. (1999) supra), wherein the $^{31}$P NMR chemical shifts of two diastereomers of this complex in CDCl$_3$ were reported: δ 47.3 (R$_C$, S$_P$), 43.3 (R$_C$, R$_P$). The major diastereomer produced herein showed the 47.3 ppm shift, but since the S$_C$-form of the Pd reagent was used, this corresponds to the S$_C$, R$_P$ diastereomer, and the major enantiomer of the phosphine formed in this catalytic reaction is R$_P$. Note that the S$_P$-enantiomer was favored with the Pd catalyst.

EXAMPLE 31

Reaction of Benzyl Bromide with PHPh(t-Bu) in the Absence of a Catalyst

To PHPh(t-Bu) (16.6 mg, 0.1 mmol) in 0.2 mL of THF was added NaOSiMe$_3$ (11.2 mg, 0.1 mmol) suspended in 0.3 mL of THF. The mixture was transferred to an NMR tube. Benzyl bromide (12 µL, 17 mg, 0.1 mmol) was added via microliter syringe, and the reaction mixture was monitored by $^{31}$P NMR spectroscopy. Formation of a white precipitate was observed as the reaction progressed. After 1 day the conversion was 4%.

EXAMPLE 32

Catalytic Reaction of Benzyl Bromide with PHPh(t-Bu)

To PHPh(t-Bu) (16.6 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 µL, 17 mg, 0.1 mmol) was added via microliter syringe, and the reaction mixture was monitored by $^{31}$P NMR spectroscopy. An increasing amount of white precipitate was observed as the reaction progressed. The reaction went to completion in less than 1 day. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 19 mg (74% yield) of colorless liquid (42% ee) was obtained. The tertiary phosphine was dissolved in 0.5 mL of C$_6$D$_6$ for spectroscopic characterization.

HRMS m/z calcd. for C$_{17}$H$_{22}$P$^+$ (MH$^+$) 257.1459. Found, 257.1454. $^{31}$P{$^1$H} NMR (C$_6$D$_6$): δ 10.7 (selectivity 100%). $^1$H NMR (C$_6$D$_6$): δ 7.52-7.48 (m, 2H, Ar), 7.28 (broad d, J=8, 2H, Ar), 7.15-7.04 (m, 4H, Ar), 7.02-6.97 (m, 1H, Ar), 6.95-6.92 (m, 1H, Ar), 3.16 (dd, J=14, J$_{PH}$=3, 1H, CH$_2$), 2.96 (dd, J=14, J$_{PH}$=3, 1H, CH$_2$), 0.95 (d, J$_{PH}$=12, 9H, C(CH$_3$)$_3$).

EXAMPLE 33

Reaction of Benzyl Bromide with PHPh(Is) in the Absence of a Catalyst

To an impure sample of PHPhIs (31.2 mg, 0.1 mmol) in 0.2 mL of THF was added NaOSiMe$_3$ (11.2 mg, 0.1 mmol) suspended in 0.3 mL of THF. The reaction mixture was transferred to an NMR tube. Benzyl bromide (12 µL, 17 mg, 0.1 mmol) was added via microliter syringe, and the reaction mixture was monitored by $^{31}$P NMR spectroscopy. Formation of a white precipitate was observed as the reaction progressed. After 1 day the conversion was ~60%.

EXAMPLE 34

Catalytic Reaction of Benzyl Bromide with PHPh(Is)

To an impure sample of PHPhIs (31.2 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 µL, 17 mg, 0.1 mmol) was added via microliter syringe, and the reaction mixture was monitored by $^{31}$P NMR spectroscopy. An increasing amount of white precipitate was observed as the reaction progressed. The reaction went to completion in ~1 day. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 11 mg (27% yield) of colorless liquid (22% ee) was obtained. The tertiary phosphine was dissolved in 0.5 mL of C$_6$D$_6$ for spectroscopic characterization.

HRMS m/z calcd. for C$_{28}$H$_{36}$P$^+$ (MH$^+$) 403.2555. Found, 403.2539. $^{31}$P{$^1$H} NMR (C$_6$D$_6$): δ −23.0 (selectivity 75%, other peaks δ 26.4 (major impurity, 20%), −18.0, −18.6).

Selected $^1$H NMR (C$_6$D$_6$) signals: δ 3.93-3.88 (m, 2H, CH, Is), 3.63 (dd, J=14, J$_{PH}$=2, 1H, CH$_2$), 3.52 (dd, J=14, J$_{PH}$=3, 1H, CH$_2$), 3.29-3.22 (m, 1H, CH, Is). Selected $^{13}$C{$^1$H} NMR (C$_6$D$_6$) signals: δ 35.1 (d, J=21, CH$_2$).

EXAMPLE 35

Reaction of Benzyl Bromide with PHPh(o-An) in the Absence of a Catalyst

To PHPh(o-An) (21.6 mg, 0.1 mmol) in 0.2 mL of THF was added NaOSiMe$_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. Formation of a white precipitate was observed as the reaction progressed. After 30 minutes the conversion was 24% and the selectivity 69% (other peaks at δ 22.4 and 7.8 were also observed).

EXAMPLE 36

Catalytic Reaction of Benzyl Bromide with PHPh (o-An)

To PHPh(o-An) (21.6 mg, 0.1 mmol) in 0.1 mL of THF was added NaOSiMe$_3$ (11.2 mg, 0.1 mmol) suspended in 0.2 mL of THF. The mixture was added to Pt(Me-Duphos)(Ph)(Cl) (3.1 mg, 0.005 mmol) as the catalyst precursor (5 mol %) in 0.1 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. An increasing amount of white precipitate was observed as the reaction progressed. The reaction went to completion in ~15 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 26 mg (85% yield) of colorless liquid (9% ee) was obtained. The tertiary phosphine was dissolved in 0.5 mL of C$_6$D$_6$ for spectroscopic characterization.

HRMS m/z calcd. for C$_{20}$H$_{20}$OP$^+$ (MH$^+$) 307.1252. Found, 307.1244. The protonated phosphine oxide was also observed: m/z calcd. for C$_{20}$H$_{20}$O$_2$P$^+$ (M(O)H$^+$) 323.1201. Found, 323.1194. $^{31}$P{$^1$H} NMR (C$_6$D$_6$): δ –17.7 (selectivity 97%, other peak –17.3). $^1$H NMR (C$_6$D$_6$): δ 7.55-7.52 (m, 2H, Ar), 7.38 (ddd, J=8, 2, J$_{PH}$=5, 1H, Ar), 7.25 (broad, 1H, Ar), 7.24 (broad, 1H, Ar), 7.20 (ddd, J=9, 8, 1, 1H, Ar), 7.16-7.12 (m, 5H, Ar), 7.07-7.04 (m, 1H, Ar), 6.91 (dtd, J=8, 1, J$_{PH}$=1, 1H, Ar), 6.54 (ddd, J=9, 1, J$_{PH}$=4, 1H, Ar), 3.64 (dd, J=14, J$_{PH}$=1, 1H, CH$_2$), 3.35 (dd, J=14, 1H, CH$_2$), 3.23 (3H, OCH$_3$). $^{13}$C{$^1$H} NMR (C$_6$D$_6$): δ 162.0 (d, J=12, quat), 139.1 (d, J=9, quat), 138.9 (d, J=17, quat), 134.1 (d, J=20, Ar), 133.4 (d, J=7, Ar), 130.6, 130.2, 130.1, 129.0, 128.8 (d, J=2, Ar), 128.7 (d, J=7, Ar), 126.3 (d, J=3, Ar), 121.5 (d, J=2, Ar), 111.0 (d, J=1, Ar), 55.4 (OCH$_3$), 35.1 (d, J=17, CH$_2$).

EXAMPLE 37

Reaction of Benzyl Bromide with 1,2-bis(phenylphosphino)ethane (PHPh(CH$_2$)$_2$PHPh) in the Absence of a Catalyst To 1,2-bis(phenylphosphino)ethane (12.3 mg, 0.05 mmol) in 0.2 mL of THF was added NaOSiMe$_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}$P NMR spectroscopy. Formation of a white precipitate was observed as the reaction progressed. No reaction occurred after 30 minutes.

EXAMPLE 38

Catalytic Reaction of Benzyl Bromide with 1,2-bis(phenylphosphino)ethane (PHPh(CH$_2$)$_2$PHPh)

To 1,2-bis(phenylphosphino)ethane (24.6 mg, 0.1 mmol) in 0.1 mL of THF was added NaOSiMe$_3$ (22.4 mg, 0.2 mmol) suspended in 0.2 mL of THF. The mixture was added to Pt((R,R)-i-Pr-Duphos) (Ph)(Cl) (7.3 mg, 0.01 mmol) as the catalyst precursor (5 mol %) in 0.1 mL of THF and the mixture was transferred to an NMR tube fitted with a septum. Benzyl bromide (34 mg, 24 μL, 0.1 mmol) was added via a microliter syringe. The reaction mixture was monitored by $^{31}$P NMR spectroscopy. An increasing amount of white precipitate was observed as the reaction progressed. The reaction went to completion in less than 5 min. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and a colorless viscous liquid was obtained (40 mg, 98% yield, 98% selectivity (other peaks=–11.0 (d, J=38), 32.4 (d, J=38)); 48% de (1:2.8 meso: rac ratio), 86% ee for the rac isomer. Results with the catalyst precursor Pt((R,R)-Me-Duphos) (Ph)(Cl) were similar, but gave the opposite hand of the rac product preferentially. An example of this catalysis at reduced temperature is described below.

Catalytic reaction of benzyl bromide with 1,2-bis(phenylphosphino)ethane at reduced temperature. A Schlenk flask was loaded with 1,2-bis(phenylphosphino)ethane (74 mg, 0.3 mmol) in 1 mL of THF, NaOSiMe$_3$ (67 mg, 0.6 mmol) suspended in 1 mL of THF and Pt(Me-Duphos)(Ph)(Cl) (9.4 mg, 0.015 mmol) as the catalyst precursor (2.5 mol %) in 1 mL of THF, with stirring. The flask was placed into a NaCl/ice bath at –5° C. Benzyl bromide (103 mg, 71 μL, 0.6 mmol) was added to the reaction mixture via a microliter syringe. An increasing amount of white precipitate was observed as the reaction progressed. After 4 hours the flask was placed in a refrigerator at –15° C. After 4 days, the reaction was complete as determined by $^{31}$P NMR spectroscopy. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 104 mg (81% yield) of a colorless liquid was obtained. The tertiary phosphine as a mixture of 2 diastereomers a and b (ratio a:b=1:2.8) was dissolved in 0.5 mL of C$_6$D$_6$ for spectroscopic characterization.

The product is a known compound (Hinton and Mann (1959), *J. Chem. Soc.* 2835-2843), which was previously prepared without diastereoselection or enantioselection.

HRMS m/z calcd. for C$_{28}$H$_{29}$O$_2$P$_2^+$ (MO$_2$H$^+$) 459.1643. Found, 459.1626. $^{31}$P{$^1$H} NMR (C$_6$D$_6$): δ –13.8 (a), –14.2 (b) (ratio a:b=1:2.8, de=47%). $^1$H NMR (C$_6$D$_6$): δ 7.32-7.24 (m, 4H, Ar), 7.12-7.00 (m, 10H, Ar), 6.97 (t, J=7, 2H, Ar), 6.95-6.89 (m, 4H, Ar), 2.81 (AB pattern, J=14, 2H, CH$_2$, a), 2.78 (AB pattern, J=14, 2H, CH$_2$, b), 2.77 (AB pattern, J=14, 2H, CH$_2$, a), 2.76 (AB pattern, J=14, 2H, CH$_2$, b), 1.78-1.65 (m, 2H, CH$_2$) overlapping with 1.67 (t, J$_{P-H}$=4, 2H, CH$_2$). $^{13}$C{$^1$H} NMR (C$_6$D$_6$): δ 138.7-138.4 (m, quat), 133.7-133.2 (m, Ar), 129.84-129.78 (m, Ar), 129.49 (b), 129.46 (a), 129.0-

128.8 (m, Ar), 126.4-126.3 (m, Ar), 37.0 (dd, J=18, 11, $CH_2$, b), 36.6 (dd, J=18, 10, $CH_2$, a), 23.89-23.8 (m, $CH_2$, a), 23.8-23.7 (m, $CH_2$, b).

The ee was determined using the general method ($^{31}P\{^1H\}$ NMR ($C_6D_6$): δ 39.0 ($b_1$), 38.7 ($a_1$), 38.0 ($a_2$), 37.7 ($b_2$), 47% de (rac:meso, 91% ee for the rac isomer).

Catalytic Reaction of Benzyl Bromide with 1,2-bis(phenylphosphino) ethane (PHPh $(CH_2)_2$PHPh). To 1,2-bis(phenylphosphino)ethane (24.6 mg, 0.1 mmol) in 0.1 mL of THF was added $NaOSiMe_3$ (22.4 mg, 0.2 mmol) suspended in 0.2 mL of THF. The mixture was added to Pt((R,R)-i-Pr-Duphos)(Ph)(Cl) (7.3 mg, 0.01 mmol) as the catalyst precursor (5 mol %) in 0.1 mL of THF and the mixture was transferred to an NMR tube fitted with a septum. Benzyl bromide (34 mg, 24 μL, 0.1 mmol) was added via a microliter syringe. The reaction mixture was monitored by $^{31}P$ NMR spectroscopy. An increasing amount of white precipitate was observed as the reaction progressed. The reaction went to completion in less than 5 min. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and a colorless viscous liquid was obtained (40 mg, 98% yield, 98% selectivity (other peaks =−11.0 (d, J=38), 32.4 (d, J=38)); 48% de (1:2.8 meso:rac ratio), 86% ee for the rac isomer. Results with the catalyst precursor Pt((R,R)-Me-Duphos) (Ph)(Cl) were similar, but gave the opposite hand of the rac product preferentially. An example of this catalysis at reduced temperature is described below.

Catalytic reaction of benzyl bromide with 1,2-bis(phenylphosphino)ethane at reduced temperature. A Schlenk flask was loaded with 1,2-bis(phenylphosphino)ethane (74 mg, 0.3 mmol) in 1 mL of THF, $NaOSiMe_3$ (67 mg, 0.6 mmol) suspended in 1 mL of THF and Pt(Me-Duphos)(Ph)(Cl) (9.4 mg, 0.015 mmol) as the catalyst precursor (2.5 mol %) in 1 mL of THF, with stirring. The flask was placed into a NaCl/ice bath at −5° C. Benzyl bromide (103 mg, 71 μL, 0.6 mmol) was added to the reaction mixture via a microliter syringe. An increasing amount of white precipitate was observed as the reaction progressed. After 4 hours the flask was placed in a refrigerator at −15° C. After 4 days, the reaction was complete as determined by $^{31}P$ NMR spectroscopy. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 104 mg (81% yield) of a colorless liquid was obtained. The tertiary phosphine as a mixture of 2 diastereomers a and b (ratio a:b=1:2.8) was dissolved in 0.5 mL of $C_6D_6$ for spectroscopic characterization.

HRMS m/z calcd. for $C_{28}H_{29}O_2P_2^+$ ($MO_2H^+$) 459.1643. Found, 459.1626. $^{31}P\{^1H\}$ NMR ($C_6D_6$): δ −13.8 (a), −14.2 (b) (ratio a:b=1:2.8, de=47%). $^1H$ NMR ($C_6D_6$): δ 7.32-7.24 (m, 4H, Ar), 7.12-7.00 (m, 10H, Ar), 6.97 (t, J=7, 2H, Ar), 6.95-6.89 (m, 4H, Ar), 2.81 (AB pattern, J=14, 2H, $CH_2$, a), 2.78 (AB pattern, J=14, 2H, $CH_2$, b), 2.77 (AB pattern, J=14, 2H, $CH_2$, a), 2.76 (AB pattern, J=14, 2H, $CH_2$, b), 1.78-1.65 (m, 2H, $CH_2$) overlapping with 1.67 (t, $J_{P-H}$=4, 2H, $CH_2$). $^{13}C\{^1H\}$ NMR ($C_6D_6$): δ 138.7-138.4 (m, quat), 133.7-133.2 (m, Ar), 129.84-129.78 (m, Ar), 129.49 (b), 129.46 (a), 129.0-128.8 (m, Ar), 126.4-126.3 (m, Ar), 37.0 (dd, J=18, 11, $CH_2$, b), 36.6 (dd, J=18, 10, $CH_2$, a), 23.89-23.8 (m, $CH_2$, a), 23.8-23.7 (m, $CH_2$, b).

EXAMPLE 39

Reaction of Benzyl Bromide with 1,2-bis(phenylphosphino)propane (PHPh$(CH_2)_3$PHPh) in the Absence of a Catalyst To 1,2-bis(phenylphosphino)propane (13 mg, 0.05 mmol) in 0.2 mL of THF was added $NaOSiMe_3$ (11.2 mg, 0.1 mmol) suspended in 0.3 mL of THF. The reaction mixture was transferred to an NMR tube. Benzyl bromide (12 μL, 17 mg, 0.1 mmol) was added via microliter syringe, and the reaction mixture was monitored by $^{31}P$ NMR spectroscopy. Formation of a white precipitate was observed as the reaction progressed. After 30 minutes the conversion was 11% and the selectivity 24% (other peak δ −10.8).

EXAMPLE 40

Catalytic Reaction of Benzyl Bromide with 1,2-bis(phenylphosphino)propane (PHPh$(CH_2)_3$PHPh)

To 1,2-bis(phenylphosphino)propane (26 mg, 0.1 mmol) in 0.1 mL of THF was added $NaOSiMe_3$ (22.4 mg, 0.2 mmol) suspended in 0.2 mL of THF. The mixture was added to Pt(Me-Duphos) (Ph)(Cl) (6.2 mg, 0.01 mmol) as the catalyst precursor (5 mol %) in 0.1 mL of THF. The reaction mixture was transferred to an NMR tube. Benzyl bromide (34 mg, 24 μL, 0.2 mmol) was added via a microliter syringe. The reaction mixture was monitored by $^{31}P$ NMR spectroscopy. An increasing amount of white precipitate was observed as the reaction progressed. The reaction went to completion in less than 5 minutes. The catalyst and NaBr were removed from the reaction mixture on a silica column (5 cm height, 0.6 cm diameter), using a 9:1 petroleum ether:THF mixture as eluent. The catalyst and NaBr did not elute. The solvent was removed under vacuum and 39 mg (87% yield) of a colorless liquid was obtained. The tertiary phosphine as a mixture of 2 diastereomers a and b (ratio a:b (meso/rac)=1:3.9) was dissolved in 0.5 mL of $C_6D_6$ for spectroscopic characterization.

The product is a known compound (Yeh, et al., (1990) Phosphorus, Sulfur and Silicon and the Related Elements 47: 319-323) which was previously prepared without diastereoselection or enantioselection. The spectroscopic data provided herein were consistent with that of Yeh, et al. ((1990) supra).

$^{31}P\{^1H\}$ NMR ($C_6D_6$): δ −19.0 (a), −19.2 (b) (lit. −18.6, −19.4); ratio a:b=1:3.9, de 59%) (selectivity 100%). $^{13}C\{^1H\}$ NMR ($C_6D_6$): δ 139.1 (d, J=18, meso), 139.0 (d, J=19, rac), 138.6 (d, J=5, overlapping rac/meso), 133.31 (d, J=19, rac), 133.30 (d, J=19, meso), 129.8 (d, J=6, overlapping rac/meso), 129.4 (meso), 129.3 (rac), 128.9-128.8 (m, overlapping rac/meso), 126.4-126.3 (m, overlapping rac/meso), 37.0 (d, J=17, P—$CH_2$Ph, rac), 36.9 (d, J=17, P—$CH_2$Ph, meso), 29.3-29.1 (m, P—$CH_2$, overlapping rac/meso), 23.0 (t, J=16, $CH_2$, overlapping rac/meso). $^1H$ NMR ($C_6D_6$): δ 7.35-7.29 (m, 4H), 7.09-7.05 (m, 10H), 7.00-6.95 (m, 6H), 2.84 (1H, AB pattern, J=13, $CH_2$Ph, rac), 2.79 (1H, AB pattern, J=13, $CH_2$Ph, rac), 2.82 (1H, AB pattern, J=14, $CH_2$Ph, meso), 2.79 (1H, AB pattern, J=14, $CH_2$Ph, meso), 1.69-1.53 (m, 4H, $CH_2$, rac+meso), 1.50-1.42 (m, 2H, $CH_2$, rac+meso).

The ee was determined using the general method ($^{31}P\{^1H\}$ NMR ($C_6D_6$): δ 35.3 ($b_1$), 34.9 ($a_1$), 31.3 ($a_2$), 28.3 ($b_2$), ratio a:b=1:4, ratio $a_1$:$a_2$=1.1:1, a-meso diastereomer, ratio $b_1$:$b_2$=1:25.7, 93% ee for b)).

EXAMPLE 41

Reaction of α,α'-Dibromo-m-xylene with PHMeIs in the Absence of a Catalyst

To PHMeIs (50 mg, 0.2 mmol) in 0.1 mL of toluene was added NaOSiMe$_3$ (22.4 mg, 0.2 mmol) suspended in 0.2 mL of toluene and α,α'-dibromo-m-xylene (26.3 mg, 0.1 mmol) in 0.1 mL of toluene. The reaction mixture was transferred to an NMR tube and monitored by $^{31}$P NMR spectroscopy. Formation of a white precipitate was observed as the reaction progressed. After 1 week, conversion was ~49% and selectivity 45% (other peaks δ 35.4, 34.7, 34.6, 34.5, −53.2, −55.4, −58.7, −83.6, −84.2).

EXAMPLE 42

Catalytic Reaction of α,α'-Dibromo-m-xylene with PHMeIs

To PHMeIs (50 mg, 0.2 mmol) in 0.1 mL of toluene was added NaOSiMe$_3$ (22.4 mg, 0.2 mmol) suspended in 0.2 mL of toluene. The mixture was added to Pt(Me-Duphos)(Ph)(PMeIs) (8.3 mg, 0.01 mmol) as the catalyst precursor (5 mol %) in 0.1 mL of toluene and α,α'-dibromo-m-xylene (26.3 mg, 0.1 mmol) in 0.1 mL of toluene. The reaction mixture was transferred to an NMR tube, and the reaction mixture was monitored by $^{31}$P NMR spectroscopy. An increasing amount of white precipitate was observed as the reaction progressed. The reaction went to completion in ~24 hours. In addition to the desired product, peaks due to impurities were observed at δ 5 41.4, 40.2, 38.9, −39.9, −40.1, and −40.5.

The catalyst, NaBr and some of the impurities were removed from the reaction mixture on a silica column (14 cm height, 1 cm diameter), using a 9:1 petroleum ether:THF mixture as eluent. The catalyst, NaBr and some of the impurities did not elute. The solvent was removed under vacuum, and 52 mg (86% yield) of a colorless liquid was obtained. It was dissolved in 0.5 mL of C$_6$D$_6$ for spectroscopic characterization.

HRMS m/z calcd. for C$_{40}$H$_{61}$P$_2^+$ (MH$^+$) 603.4249. Found, 603.4227. The following NMR spectra are reported as a mixture of two diastereomers a and b (a:b (rac:meso)=3.4:1, 55% de) unless otherwise indicated. $^{31}$P{$^1$H} NMR (C$_6$D$_6$) δ −40.3 (a), −40.6 (b) (selectivity 87%, other peaks δ −39.7, −40.5 (major impurity, ca. 10% of the mixture), −41.0). $^1$H NMR (C$_6$D$_6$): δ 7.08-7.06 (m, 1H, Ar), 7.05 (d, J$_{P-H}$=2, 4H, Is, b), 7.04 (d, J$_{P-H}$=2, 4H, Is, a), 6.98 (d, J=1, 2H, Ar, a), 6.96 (d, J=2, 2H, Ar, b), 6.93 (d, J=2, 1H, Ar, a), 6.91 (1H, Ar, b), 4.10-4.00 (m, 4H, CH, i-Pr), 3.20 (dd, J$_{P-H}$=2, J=14, 1H, CH$_2$, b), 3.16 (dd, J$_{P-H}$=2, J=14, 1H, CH$_2$, a), 3.10 (d, J=14, 1H, CH$_2$, a+b overlapping), 2.75-2.64 (m, 2H, CH, i-Pr), 1.34 (d, J$_{P-H}$=7, 6H, P-Me, b), 1.30 (d, J$_{P-H}$=7, 6H, P-Me, a), 1.26 (d, J=7, 12H, CH$_3$, b), 1.25 (d, J=7, 12H, CH$_3$, a), 1.16 (d, J=7, 12H, CH$_3$, b), 1.15 (d, J=7, 12H, CH$_3$, a), 1.12-1.10 (m, 12H, CH$_3$, a+b). $^{13}$C{$^1$H} NMR (C$_6$D$_6$): δ 156.3 (d, J=13, quat, b), 156.2 (d, J=14, quat, b), 150.8 (quat), 140.3 (dd, J=10, 3, quat, Ar), 131.2 (d, J=26, b), 131.1 (d, J=26, a), 130.7 (t, J=6, Ar), 130.6 (d, J=7, Ar), 129.1 (m, Ar), 128.9 (m, Ar), 127.3-127.2 (m, Ar), 126.9 (d, J=6, Ar), 122.8 (Ar), 122.6 (d, J=4, Is), 37.2 (d, J=19, CH, i-Pr, a), 37.1 (d, J=19, CH, i-Pr, b), 35.01 (CH, i-Pr, b), 34.99 (CH, i-Pr, a), 31.9 (d, J=21, CH$_2$, b), 31.8 (d, J=21, CH$_2$, a), 25.50 (CH$_3$, b), 25.49 (CH$_3$, a), 25.4 (CH$_3$, a), 24.8 (CH$_3$, b), 24.44 (CH$_3$, a), 24.45 (CH$_3$, b), 11.92 (d, J=22, P-Me, b), 11.88 (d, J=21, P-Me, a). The ee was determined using the general method ($^{31}$P{$^1$H} NMR (C$_6$D$_6$): δ 15.0 (b$_1$), 14.1 (b$_2$), 14.0 (a$_1$), 12.2 (a$_2$), ratio a:b=3.8:1, ratio a$_1$:a$_2$=1: 5.4, 69% ee for a, b-meso diastereomer, ratio b$_1$:b$_2$=1:1).

EXAMPLE 43

Reaction of 2,6-bis(bromomethyl)pyridine with PHMeIs in the Absence of a Catalyst To PHMeIs (25 mg, 0.1 mmol) in 0.1 mL of toluene was added NaOSiMe$_3$ (11.2 mg, 0.1 mmol) suspended in 0.2 mL of toluene and 2,6-bis(bromomethyl)pyridine (13.2 mg, 0.05 mmol) in 0.1 mL of toluene. The reaction mixture was transferred to an NMR tube and monitored by $^{31}$P NMR spectroscopy. Formation of a white precipitate was observed as the reaction progressed. After 4 days, conversion was ca. 22% and selectivity 52% (other peaks δ38.4, −40.6, −41.4, −53.1, −56.2).

EXAMPLE 44

Catalytic Reaction of 2,6-bis(bromomethyl)pyridine with PHMeIs

To PHMeIs (50 mg, 0.2 mmol) in 0.1 mL of toluene was added NaOSiMe$_3$ (22.4 mg, 0.2 mmol) suspended in 0.2 mL of toluene. The mixture was added to Pt(Me-Duphos)(Ph)(PMeIs) (8.3 mg, 0.01 mmol) as the catalyst precursor (5 mol %) in 0.1 mL of toluene and 2,6-bis(bromomethyl)pyridine (26.4 mg, 0.1 mmol) in 0.1 mL of toluene. The reaction mixture was transferred to an NMR tube and monitored by $^{31}$P NMR spectroscopy. An increasing amount of white precipitate was observed as the reaction progressed. The reaction went to completion in ~1 day. Formation of impurities, presumed to be phosphonium salts (δ 40.3, 40.1, 39.9, 39.7, 38.9, 38.4, 13% total) was observed. The catalyst, phosphonium salts and NaBr were removed from the reaction mixture on a silica column (5 cm height, 0.6 cm diameter), using a 9:1 petroleum ether:THF mixture as eluent. The catalyst, phosphonium salts and NaBr did not elute. The solvent was removed under vacuum and 55 mg (90% yield) of colorless liquid was obtained. The phosphine was dissolved in 0.5 mL of C$_6$D$_6$ for spectroscopic characterization.

HRMS m/z calcd. for C$_{39}$H$_{60}$NP$_2$O$_2^+$ (MO$_2$H$^+$) 636.4099. Found, 636.4083. The mono-oxidized and protonated product was also observed: m/z 620.4127 (calcd. for C$_{39}$H$_{60}$NP$_2$O$_2^+$ (MOH$^+$) 620.4150).

The following NMR spectra are reported as a mixture of two diastereomers a and b (a:b=1.4:1 (rac/meso), 17% de) unless otherwise indicated. $^{31}$P{$^1$H} NMR (C$_6$D$_6$): δ −40.8 (a), −40.9 (b) (selectivity 90%, other peak δ −41.4). $^1$H NMR (C$_6$D$_6$): δ 7.12 (d, J$_{P-H}$=2, 4H, Is, b), 7.10 (d, J$_{P-H}$=2, 4H, Is, a), 7.03-6.94 (m, 1H, Ar), 6.83 (t, J$_{P-H}$=1, 1H, Ar, a), 6.81 (t, J$_{P-H}$=2, 1H, Ar, b), 6.77 (t, J$_{P-H}$=2, 1H, Ar, a), 6.75 (t, J$_{P-H}$=2, 1H, Ar, b), 4.22-4.14 (m, 4H, CH, i-Pr), 3.65 (d, J=13, 1H, CH$_2$, b), 3.59 (d, J=13, 1H, CH$_2$, a), 3.37 (dd, J=13, J$_{PH}$=2, 1H, CH$_2$, a), 3.32 (dd, J=13, J$_{PH}$=2, 1H, CH$_2$, b), 2.82-2.70 (m, 2H, CH, i-Pr), 1.58 (d, J=7, 3H, P—CH$_3$, b), 1.45 (d, J=7, 3H, P—CH$_3$, a), 1.33 (d, J=7, 12H, CH$_3$, a), 1.32 (d, J=7, 12H, CH$_3$, b), 1.26-1.21 (m, 12H, CH$_3$), 1.18 (d, J=7, 12H, CH$_3$, b), 1.17 (d, J=7, 12H, CH$_3$, a). $^{13}$C{$^1$H} NMR (C$_6$D$_6$): δ 160.4 (d, J=11, quat, b), 160.3 (d, J=12, quat, a), 156.2 (d, J=14, quat, a+b overlapping), 150.8 (dd, J=5, 1, quat), 136.7 (m, Ar), 136.5 (Ar), 131.7 (d, J=26, Ar), 131.5 (d, J=26, Ar), 122.7 (Ar), 122.6 (d, J=4, Is), 120.8-120.6 (m, Ar), 120.5-120.4 (m, Ar), 39.7 (d, J=19, CH, i-Pr, a), 39.6 (d, J=19, CH, i-Pr, b), 35.1 (CH, i-Pr, b), 35.0 (d, J=3, CH, i-Pr, a), 31.92 (d, J=22, CH$_2$, b), 31.88 (d, J=22, CH$_2$, a), 25.52 (CH$_3$, b), 25.51 (CH$_3$, a), 25.4 (CH₃, a), 25.39 (CH₃, b), 24.8 (CH₃, b), 24.4 (CH₃, a), 12.1 (d, J=21, P-Me, b), 12.0 (d, J=21, P-Me, a).

The ee was determined using the general method: ($^{31}$P{$^1$H} NMR (C₆D₆): δ 14.3 (a₁), 13.3 (a₂), 12.5 (b₁), 12.2 (b₂), ratio a:b=1.4:1, ratio a₁:a₂=6.2:1, 72% ee for a, b-meso diastereomer, ratio b₁:b₂=1.1:1).

EXAMPLE 45

Screening Chiral Diphosphine Ligands with In Situ Precatalyst Formation in the Catalytic Reaction of benzyl bromide with 1,2-bis(phenylphosphino)ethane To a diphosphine (0.2 mL of 0.05 mM THF solution, 0.01 mmol), Pt(COD)(R)Cl (100 μL of a 0.1 M solution in THF, 0.01 mol, R=Me or Ph) was added. After 15 minutes, 1,2-bis (phenylphosphino)ethane (50 μL of 2.0 M solution in THF, 0.1 mmol) was added and the solution became cloudy. NaO-SiMe₃ (0.2 mL of 1.0 M solution in THF, 0.2 mmol) was added and the solution became yellow. The reaction mixture was transferred to an NMR tube. Benzyl bromide (24 μL, 34 mg, 0.2 mmol) was added via microliter syringe, and formation of a white precipitate was immediately observed. The reaction mixture was monitored by $^{31}$P NMR spectroscopy, which enabled determination of the extent of conversion and the rac/meso ratio of the product diphosphine.

The reaction time and de for Pt-catalyzed asymmetric alkylation of 1,2-bis(phenylphosphino)ethane with benzyl bromide using catalysts generated in situ from Pt(COD)(R)(Cl) and a chiral diphosphine (diphos*) are provided in Table 6. Time for complete conversion of the disecondary phosphine substrate and the rac/meso ratio were determined by $^{31}$P NMR spectroscopy.

TABLE 6

| Diphos* | Time, de (R = Me) | Time, de (R = Ph) |
|---|---|---|
| (S)-Tol-BINAP | <2.5 hours, 3 | <2 hours, 7 |
| (R)-BINAP | <2.5 hours, 6 | <2 hours, 4 |
| (R,S)-CyPF-t-Bu | <2.5 hours, 6 | <30 minutes, 11 |
| (R,S)-PPF-t-Bu | <2.5 hours, 3 | <2 hours, 4 |
| (S)-BoPhoz | <2.5 hours, 4 | |
| (S,S)-Et-FerroTANE | <2.5 hours, 3 | <2 hours, 3 |
| (S,S)-Chiraphos | <1.5 hours, 3 | <2 hours, 5 |
| (R,R)-Me-Duphos | <2.5 hours, 9 | <30 minutes, 33 |
| (R,R)-Et-Duphos | <2.5 hours, 11 | <30 minutes, 35 |
| (S,S)-i-Pr-Duphos | <2.5 hours, 9 | <30 minutes, 31 |
| (S,S)-DIOP | <2.5 hours, 4 | <2 hours, 4 |

EXAMPLE 46

Screening Benzyl Halides in Pt-Catalyzed Asymmetric Alkylation of 1,2-bis(phenylphosphino)ethane 50 μL (0.01 mmol) of a stock solution of 0.2 M Pt((R,R)-Me-Duphos) (Ph)(Cl) in THF was charged to an NMR tube. The disecondary phosphine (50 μL of a 2.0 M solution in THF, 0.1 mmol) was added via syringe and a white precipitate was observed. NaOSiMe₃ (200 μL of a 1.0 M solution in THF (Aldrich), 0.2 mmol) was added; the precipitate dissolved and the solution turned yellow. The benzyl halide (0.2 mmol) was added (neat, for liquids, or as a solution in the minimum amount of dry THF, about 100 μL) and a white precipitate formed. The reaction was monitored by $^{31}$P NMR spectroscopy.

Time for complete conversion, de, and $^{31}$P NMR data for the products Ph(CH₂Ar)PCH₂CH₂PPh(CH₂Ar) formed in Pt-catalyzed alkylation of 1,2-bis(phenylphosphino)ethane with benzyl halides using the catalyst precursor Pt((R,R)-Me-Duphos)(Ph)(Cl) is provided in Table 7.

TABLE 7

| Benzyl Halide | Time (h)[a] | de (%) | $^{31}$P NMR (δ)[b] |
|---|---|---|---|
| benzyl bromide | <18 | 23 | −13.1, −13.6 |
| 2-(trifluoromethyl)benzyl bromide | <1 | 66 | −17.1 (br)[c] |
| 4-(trifluoromethyl)benzyl bromide | <1 | 4 | −16.5, −17.1[e] |
| 3,5-bis(trifluoromethyl)benzyl bromide | <1 | 6 | −16.0, −16.9[e] |
| 4-methoxybenzyl bromide | <18 | 21 | −13.8, −14.2[d] |
| 3,5-di-tert-butylbenzyl bromide | <1 | 12 | −19.5, −19.7[d] |
| 2-phenylbenzyl bromide | <1 | 4 | −16.1, −16.7[e] |

TABLE 7-continued

| Benzyl Halide | Time (h)[a] | de (%) | 31P NMR (δ)[b] |
|---|---|---|---|
| pentafluorobenzyl bromide (C6F5-CH2Br) | <1 | 36 | −19.4, −20.2 |
| 2-cyanobenzyl bromide | <1 | 37 | −17.4, −17.8 |
| 2-iodobenzyl bromide | <1 | 25 | −21.2, −21.7 |
| 2-(bromomethyl)naphthalene | <1 | 33 | −20.4, −20.9[d] |
| 1-(chloromethyl)naphthalene | <18 | 25 | −15.6, −16.1 |
| 9-(chloromethyl)anthracene | <2.5 | 97 | −15.7, −16.0 |
| 2-methylbenzyl bromide | <1 | 28 | −23.0, −23.4[e] |
| 2,4-bis(trifluoromethyl)benzyl bromide | <8 | 55 | −14.6 (br)[f] |
| 2-methyl-1-(chloromethyl)naphthalene | <24 | 29 | −17.9, −18.1[e] |

[a] The time for conversion of the disecondary phosphine substrate and the de were determined by 31P NMR spectroscopy.
[b] In THF (crude reaction mixture); 85% $H_3PO_4$ internal standard. The chemical shift of the minor diastereomer is listed first
[c] Additional 19F NMR data: δ −65.5 (major), −66.0 (minor), −68.2 (trace); integration of the 19F NMR spectrum was used to determine the de
[d] Formation of byproducts was observed.
[e] The 31P NMR signals were not baseline resolved
[f] Additional 19F NMR data: δ −65.0 (major ortho $CF_3$), −65.5 (minor ortho $CF_3$), −67.7, −68.9 (overlapping meta $CF_3$); integration of the 19F NMR spectrum was used to determine the de.

EXAMPLE 47

Screening Benzyl Halides in Pt-Catalyzed Asymmetric Alkylation of 1,2-bis(phenylphosphino)propane 50 μL (0.005 mmol) of a stock solution of 0.1 M Pt((R,R)-Me-Duphos)(Ph)(Cl) in THF was charged to an NMR tube. The disecondary phosphine (50 μL of a 2.0 M solution in THF, 0.1 mmol) was added via syringe; a white precipitate was observed. $NaOSiMe_3$ (200 μL of a 1.0 M solution in THF (Aldrich), 0.2 mmol) was added; the precipitate dissolved and the solution turned yellow. The benzyl halide (0.2 mmol) was added (neat, for liquids, or as a solution in the minimum amount of dry THF, about 100 μL) and a white precipitate formed. The reaction was monitored by 31P NMR spectroscopy.

Time for complete conversion, de, and 31P NMR data for the products $Ph(CH_2Ar)PCH_2CH_2CH_2PPh(CH_2Ar)$ formed in Pt-catalyzed alkylation of 1,2-bis(phenylphosphino) propane with benzyl halides using the catalyst precursor Pt((R,R)-Me-Duphos)(Ph)(Cl) is provided in Table 8.

TABLE 8

| Benzyl Halide | Time (h)[a] | de (%) | 31P NMR (δ)[b] |
|---|---|---|---|
| benzyl bromide | <1 | 63 | −16.5, −16.6 |
| 2-(trifluoromethyl)benzyl bromide | <1 | 80 | −15.8 (q, J = 13)[c] |

TABLE 8-continued

| Benzyl Halide | Time (h)[a] | de (%) | ³¹P NMR (δ)[b] |
|---|---|---|---|
| 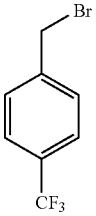 4-CF₃-C₆H₄-CH₂Br | <1 | 63 | −17.1, −17.2 |
| 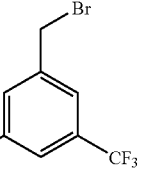 3,5-(CF₃)₂-C₆H₃-CH₂Br | >6 | 19 | −16.6, −16.8[e] |
| 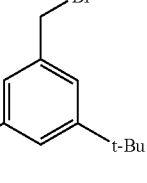 3,5-(t-Bu)₂-C₆H₃-CH₂Br | <1 | 40 | −19.1, −19.2[d] |
| 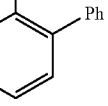 2-Ph-C₆H₄-CH₂Br | >6 | 60 | −16.4, −16.3[e] |
| 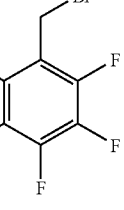 C₆F₅-CH₂Br | >24 | nd[f] | −17.8 (Apparent t, J = 13) |
| 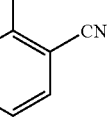 2-CN-C₆H₄-CH₂Br | <1 | 44 | −15.1, −15.0[e] |
| 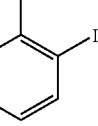 2-I-C₆H₄-CH₂Br | <1 | 54 | −19.26, −19.34[e] |
| 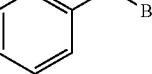 2-naphthyl-CH₂Br | <1 | 48 | −18.5, −18.6[d] |
| 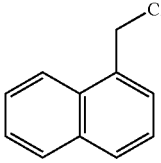 1-naphthyl-CH₂Cl | <1 | 37 | −20.7, −20.9[d] |
| 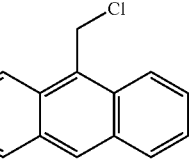 9-anthracenyl-CH₂Cl | <1 | 18 | −14.8, −14.9[e] |
| 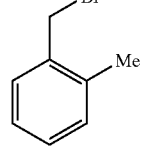 2-Me-C₆H₄-CH₂Br | <4 | 17 | −23.15, −23.24[e,d] |
| 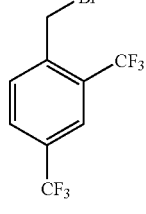 2,4-(CF₃)₂-C₆H₃-CH₂Br | >6 | nd[f] | −13 (br m)[d,g] |
| 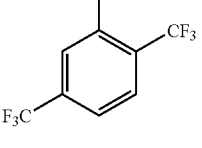 2,5-(CF₃)₂-C₆H₃-CH₂Br | <6 | 80 | −12.2 (br), −13.9 (br)[d] |
| 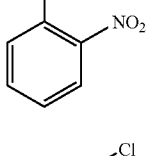 2-NO₂-C₆H₄-CH₂Br | >>6[h] | nd[f] | −16.4 |
| 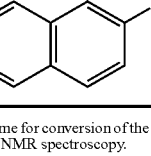 2-Me-naphthyl-CH₂Cl | <1 | 37 | −19.0, −19.1[e] |

[a] The time for conversion of the disecondary phosphine substrate and the de were determined by ³¹P NMR spectroscopy.
[b] In THF (crude reaction mixture); 85% H₃PO₄ internal standard. The chemical shift of the minor diastereomer is listed first
[c] Additional ¹⁹F NMR data: δ −64.5 (major), −65.1 (minor); integration of the ¹⁹F NMR spectrum was used to determine the de
[d] Formation of byproducts was observed.
[e] The ³¹P NMR signals were not baseline resolved
[f] nd = not determined
[g] Additional ¹⁹F NMR data: δ −65.2, −65.8 and −68.0 (minor), −69.2.
[h] Reaction did not go to completion

EXAMPLE 48

Pt-Catalyzed Asymmetric Synthesis of 1,2-bis-((anthracen-9-methyl)(phenyl)phosphino)ethane To 1,2-bis(phenylphosphino)ethane (0.8 mmol, 197 mg) dissolved in 2 mL of THF, NaOSiMe$_3$ (1.6 mmol, 1.6 mL of a 1.0 M solution in THF) and Pt((R,R)-Me-Duphos)(Ph)(Cl) (0.10 mmol, 49 mg) were added; the solution turned yellow. A solution of 9-(chloromethyl)anthracene (1.6 mmol, 363 mg) in 2 mL of THF was added. The solution immediately turned orange and a white precipitate formed within 5 min. The mixture was stirred overnight, then filtered through Celite, washing with THF to remove the salt. However, the Celite remained yellow even after washing. The solvent was removed from the filtrate in vacuo to give approximately 300 mg of an orange solid, which was dissolved in a 1:1 mixture of petroleum ether/THF and passed through a 35 mm wide frit filled 25 mm high with silica gel. The pale yellow filtrate was concentrated under vacuum and the resulting solid was recrystallized from THF/petroleum ether at −40° C. The pale yellow supernatant was decanted to give 130 mg of yellow solid (30%). The silica plug was washed with 20 mL (each) of THF, petroleum ether, toluene, CH$_2$Cl$_2$, and diethyl ether to give 20 mg more yellow solid. However, the silica plug remained yellow even after the sequential washings, suggesting that some product may remain insoluble, explaining the low yield.

The product (30 mg, 0.048 mmol) was dissolved in 1 mL of CH$_2$Cl$_2$ and a solution of the reporter complex [Pd(NMe$_2$CH(Me)C$_{12}$H$_6$)(μ-Cl)]$_2$ (35 mg, 0.053 mmol) in 1 mL of CH$_2$Cl$_2$ was added. The solution was transferred to a NMR tube. Integration of the $^{31}$P {$^1$H} NMR spectrum showed the ee to be 70%: δ 38.6 (major), 34.6 (minor).

$^{31}$P{$^1$H} NMR (C$_6$D$_6$): δ −11.1 (rac). From the crude reaction mixture, $^{31}$P{$^1$H} NMR (THF): δ −15.7 (meso), −16.0 (rac). $^1$H NMR (CDCl$_3$): δ 8.28 (2H, Ar), 8.03 (d, J=8, 4H, Ar), 7.94 (d, J=7, 4H, Ar), 7.42-7.32 (m, 14H, Ar), 7.29-7.26 (m, 4H, Ar), 3.99 (d, J=14, 2H, benzyl H), 3.77 (d, J=14, 2H, benzyl H), 1.89-1.84 (m, 2H, CH$_2$), 1.59-1.54 (m, 2H, CH$_2$). $^{13}$C{$^1$H} NMR (C$_6$D$_6$): δ 138.5 (m, Ar), 133.0 (m, Ar), 132.0 (Ar), 130.8 (m, Ar), 130.4 (m, Ar), 129.3 (Ar), 129.1 (Ar), 128.5 (t, J=3, Ar), 126.3 (Ar), 125.5 (Ar), 125.2 (Ar), 125.0 (Ar), 29.8 (m, benzyl C), 24.2 (apparent t, J=34, CH$_2$)

EXAMPLE 49

Pt-Catalyzed Asymmetric Synthesis of 1,2-bis-((o-trifluorobenzyl)(phenyl)phosphino)ethane 1,2-bis(phenylphosphino)ethane (0.81 mmol, 200 mg) was dissolved in 2 mL of THF, and NaOSiMe$_3$ (1.6 mmol, 1.6 mL of a 1.0 M solution in THF) and Pt((R,R)-Me-Duphos) (Ph)(Cl) (0.05 mmol, 25 mg, 3 mol %) were added, turning the mixture yellow. 1-(bromomethyl)-2-(trifluoromethyl)benzene (1.6 mmol, 387 mg) was dissolved in 2 mL of THF and added to the mixture. Within five minutes, the solution turned a darker yellow and a white precipitate was observed. The mixture was stirred overnight and then filtered through Celite to remove the insoluble salt and yield a yellow solution. The solution was pumped down to give an orange oil, which was passed through a 5 mm wide, 50 mm high silica column eluting with 9:1 petroleum ether:THF to give a colorless solution. Removing the solvent under vacuum gave 240 mg of a colorless oil (crude yield 53%, 0.43 mmol).

This crude material was dissolved in 5 mL of THF and cooled to 0° C. before BH$_3$(SMe$_2$) (0.47 mmol, 0.234 mL of 2.0 M solution in THF) was added via syringe. The mixture was stirred for one hour and then volatile materials were removed in vacuo. The white solid was then dissolved in CH$_2$Cl$_2$ and passed through a silica plug column. Pumping down the solution gave 300 mg of a white solid. The solid was then dissolved in CH$_2$Cl$_2$ and layered with petroleum ether. The solution was refrigerated for 48 hours at 0° C. and white crystals formed. Yield: 250 mg, 99% (50% yield from the starting phosphine). This material was highly diastereomerically and enantiomerically enriched (>99% de, >99% ee).

HRMS m/z calcd. for C$_{30}$H$_{32}$B$_2$F$_6$P$_2$ (MH$^+$) m/z 590.2070. Found, 590.2053. Anal. Calcd. for C$_{30}$H$_{32}$B$_2$F$_6$P$_2$: C, 61.06; H, 5.47. Calcd. for C$_{30}$H$_{32}$B$_2$F$_6$P$_2$(CH$_2$Cl$_2$)$_{0.12}$: C, 60.26; H, 5.41; Found: C, 60.22; H, 5.37. $^{31}$P{$^1$H} NMR (C$_6$D$_6$): δ 22.8 (br). $^{19}$F{$^1$H} NMR (CDCl$_3$): δ −58.6 (major peak, 94% by integration), −58.8 (d, J$_{CF}$=274, $^{13}$C satellite); minor peaks at −58.68 (2.5%), −58.71 (2.7%), −59.1 (0.4%). $^1$H NMR (CDCl$_3$): δ 7.57 (d, J=8, 2H, Ar), 7.52-7.46 (m, 8H, Ar), 7.39 (t, J=7, 6H, Ar), 7.35 (t, J=8, 2H, Ar), 5.31 (CH$_2$Cl$_2$, 0.1 eq), 3.51-3.46 (m, 2H, benzyl CH$_2$), 3.40-3.35 (m, 2H, benzyl CH$_2$), 1.97-1.92 (m, 2H, CH$_2$), 1.88-1.85 (m, 2H, CH$_2$) 1.1-0.4 (br, 6H, BH$_3$). $^{13}$C{$^1$H} NMR (C$_6$D$_6$): δ 132.7 (t, J=2, Ar), 132.5 (t, J=5, Ar), 131.8 (Ar), 131.7 (Ar), 131.4 (Ar), 129.0 (t, J=5, Ar), 128.3 (Ar), 127.5 (d, J=51, Ar), 127.2 (Ar), 126.4 (q, J=6), 124.7 (q, J=274, CF$_3$), 30.8 (d, J=29, benzyl C, batman splitting pattern), 18.7 (d, J=35, CH$_2$, batman splitting pattern).

NMR data for the meso diphosphine-borane: $^{31}$P{$^1$H} NMR (C$_6$D$_6$): δ 22.9 (br). $^{19}$F{$^1$H} NMR (C$_6$D$_6$): δ −58.4, −58.6 (d, J=274, $^{13}$C satellite). $^1$H NMR (C$_6$D$_6$): δ 7.61-7.57 (m, 4H, Ar), 7.13 (d, J=8, 2H, Ar), 7.09 (d, J=8, 2H, Ar), 6.98-6.84 (m, Ar, 8H), 6.64 (t, J=8, Ar, 2H), 3.15-3.10 (m, 2H, benzyl CH$_2$), 2.98-2.93 (m, 2H, benzyl CH$_2$), 2.50-2.46 (m, 2H, CH$_2$), 1.67-1.65 (m, 2H, CH$_2$), 1.8-1.2 (br m, BH$_3$, 6H). $^{13}$C{$^1$H} NMR (CDCl$_3$): δ 132.6 (t, J=5, Ar), 132.5 (m, Ar), 132.4-132.3 (m, Ar), 132.2-131.8 (m, Ar), 131.76 (Ar), 130.9 (Ar), 129.1 (t, J=5, Ar), 129.0 (Ar), 127.46 (Ar), 126.6-126.4 (m, Ar), 126.2 (Ar), 125.8 (Ar), 124.06 (q, J=274, CF$_3$), 31.3-31.1 (m, batman splitting, benzyl C), 18.2-17.6 (m, batman splitting, CH$_2$). Overlap in the $^{13}$C NMR spectra precluded assignment of rac/meso signals in some cases.

EXAMPLE 50

Chromatography-free Synthesis of the Borane Adduct of 1,2-bis-((o-trifluorobenzyl) (phenyl)phosphino)ethane and its Deprotection to yield 1,2-bis-((o-trifluorobenzyl)(phenyl)phosphino)ethane 1,2-bis(phenylphosphino)ethane (0.27 mmol, 66 mg) was dissolved in 5 mL of THF, and solutions of NaOSiMe$_3$ (0.54 mmol, 60 mg) in 5 mL of THF and Pt((R,R)-i-Pr-Duphos) (Ph)(Cl) (0.02 mmol, 15 mg, 5 mol %) in 3 mL of THF were added, turning the mixture yellow. A solution of 1-(bromomethyl)-2-(trifluoromethyl)benzene (0.54 mmol, 128 mg) in 3 mL of THF was added, and the color immediately turned orange-red. After stirring overnight, the peach-colored solution was cooled to 0° C. and BH$_3$(SMe$_2$) (0.56 mmol, 0.28 mL of 2.0 M THF solution) was added via syringe. The mixture was stirred for one hour at 0° C., and then allowed to warm to room temperature overnight. The resulting white slurry was filtered through Celite, eluting with CH$_2$Cl$_2$. The solvent was removed in vacuo to yield a white solid, which was recrystallized from methylene chloride/petroleum ether at 0° C. to yield 130 mg (85%) of white crystals of 85% de (from integration of the $^{19}$F NMR spectrum). The filtrate from the recrystallization was enriched in the meso diastereomer (13% de (rac/meso)).

Deprotection of the Diphosphine-Borane. The borane adduct (32 mg, 0.054 mmol) was stirred in 5 mL of THF and DABCO (18 mg, 0.16 mmol), dissolved in 5 mL of THF, was added. The mixture was stirred for 48 hours and monitored by $^{31}$P NMR spectroscopy; deprotection was not complete after 24 hours. The THF was removed in vacuo, and the resulting oil was dissolved in petroleum ether and filtered through a silica column (15 by 1 mm) eluting with 7×15 mL fractions of petroleum ether to remove excess amine. Then the phosphine was eluted with 3×15 mL fractions of $CH_2Cl_2$. The solvent was removed in vacuo to give 30 mg (98% yield) of a colorless solid.

$^{31}P\{^1H\}$ NMR ($C_6D_6$): δ −11.8 (m, $J_{PP}$=30.8, $J_{PF}$=15.0, −0.4, $J_{FF}$=−3.3). $^{19}F\{^1H\}$ NMR ($C_6D_6$): δ −59.0 (m, $J_{PP}$=30.8, $J_{PF}$=15.0, −0.4, $J_{FF}$=−3.3), extra peak at −58.4 (~1%), −59.1 (d of m, $J_{CF}$=275, $^{13}$C satellites). $^1$H NMR ($C_6D_6$): δ 7.38-7.31 (m, 6H, Ar), 7.09-7.04 (m, 6H, Ar), 6.94-6.83 (m, 4H, Ar), 6.73 (q, J=7, 2H, Ar), 3.16-3.09 (m, 2H), 3.02-2.94 (m, 2H), 1.87-1.83 (m, 2H), 1.74-1.69 (m, 2H). $^{13}C\{^1H\}$ NMR ($C_6D_6$) δ 137.7-137.5 (m, Ar), 133.4-133.1 (m, Ar), 133.2-133.1 (m, Ar), 131.8-131.7 (m, Ar), 131.5 (Ar), 129.5 (d, J=5, Ar), 128.8-128.7 (m, Ar), 126.3 (quintet, J=6, Ar), 126.0 (Ar), 125.8 (Ar), 125.2 (q, J=274, $CF_3$), 34.0-33.8 (m, batman splitting), 33.6-33.4 (m, batman splitting).

The ee of the diphosphine was determined using either a slight excess of the Pd reporter complex (S)-[Pd(NMe$_2$CH(Me)C$_{10}$H$_6$)(μ-Cl)]$_2$ in C$_6$D$_6$, to ensure monodentate coordination of the diphosphine, or with 0.5 equiv of the Pd complex in CD$_2$Cl$_2$, to favor bidentate coordination (some monodentate coordination also occurred under these conditions). Integration of the $^{31}$P and $^{19}$F NMR spectra gave the ee of the diphosphine (see Table 9 for the NMR data). Using highly rac-enriched diphosphine-borane gave material of >99% de and ee. $^{31}$P and $^{19}$F NMR data for diastereomeric complexes of the diphosphine PhP(CH$_2$o-C$_6$H$_4$CF$_3$)CH$_2$CH$_2$PPh(CH$_2$o-C$_6$H$_4$CF$_3$) with the chiral Pd reporter complex (S)-[Pd(NMe$_2$CH(Me)C$_{10}$H$_6$) (μ-Cl)]$_2$ are provided in Table 9.

TABLE 9[a]

| Monodentate Complex | RR | SS | meso |
|---|---|---|---|
| δ ($^{31}$P) (C$_6$D$_6$) | 38.6 | 38.7 | 39.2, 38.0[b] |
| δ ($^{31}$P) (CD$_2$Cl$_2$) | 38.2 | 37.8 | 38.5, 36.4[c] |
| δ ($^{19}$F) (C$_6$D$_6$) | −57.9 | −58.5[d] | −57.5, −59.3 |
| δ ($^{19}$F) (CD$_2$Cl$_2$) | −58.6 | −59.0[e] | −58.1, −59.7 |

| Chelate complex | RR | SS | meso[h] |
|---|---|---|---|
| δ ($^{31}$P) (CD$_2$Cl$_2$) | 65.4, 35.5[f] | 65.0, 37.2[g] | 66.2, 39.2[i] 65.0, 37.4[j] |
| δ ($^{19}$F) (CD$_2$Cl$_2$) | −58.1, −59.1 | −58.1, −59.1 | −57.9, −58.2[i] −58.0, −58.3 |

[a]Chemical shifts are in ppm, coupling constants in Hz.
[b]AB pattern; both peaks are doublets with J = 52
[c]AB pattern; both peaks are doublets with J = 51
[d]The $^{13}$C satellite peak was observed at δ −58.7 (d, J = 274)
[e]The $^{13}$C satellite peak was observed at δ −59.1 (d, J = 274)
[f]broad doublets, J = 22
[g]doublets, J = 24
[h]Two diastereomers of the meso chelate complex were observed.
[i]Broad peaks
[j]doublets, J = 23

What is claimed is:

1. A method for preparing an enantioenriched phosphorus-stereogenic, tertiary phosphine comprising contacting, at a temperature of from −50° C. to 25° C., a secondary phosphine with an alkyl halide and base in the presence of a chiral metal catalyst thereby preparing an enantioenriched phosphorus-stereogenic, tertiary phosphine, wherein the alkyl halide comprises benzyl halide and the chiral metal catalyst comprises Pt(chiral ligand)(Y)(Z), wherein Y and Z are independently linear, branched, or cyclic alkyl; aryl; or halide groups, or combinations thereof.

2. The method of claim 1 wherein said secondary phosphine and alkyl halide are present at a ratio of from 1:0.5 to 1:2 and said secondary phosphine and chiral metal catalyst are present at a ratio of from 40:1 to 10:1.

* * * * *